US011197828B2

(12) United States Patent
Højgaard

(10) Patent No.: US 11,197,828 B2
(45) Date of Patent: *Dec. 14, 2021

(54) SOLID ORAL DOSAGE FORM OF LIPOPHILIC COMPOUNDS

(71) Applicant: SOLURAL PHARMA APS, Ballerup (DK)

(72) Inventor: Bent Højgaard, Allerød (DK)

(73) Assignee: SOLURAL PHARMA APS, Ballerup (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/319,773

(22) PCT Filed: Jun. 17, 2015

(86) PCT No.: PCT/EP2015/063606
§ 371 (c)(1),
(2) Date: Jan. 13, 2017

(87) PCT Pub. No.: WO2015/193380
PCT Pub. Date: Dec. 23, 2015

(65) Prior Publication Data
US 2017/0119674 A1     May 4, 2017

(30) Foreign Application Priority Data
Jun. 19, 2014   (EP) .................................... 14173067

(51) Int. Cl.
| | |
|---|---|
| *A61K 9/20* | (2006.01) |
| *A61K 9/19* | (2006.01) |
| *A61K 38/12* | (2006.01) |
| *A61K 31/58* | (2006.01) |
| *A61K 31/337* | (2006.01) |
| *A61K 9/00* | (2006.01) |
| *A61K 9/48* | (2006.01) |
| *A61K 9/16* | (2006.01) |
| *A61K 47/44* | (2017.01) |
| *A61K 47/14* | (2017.01) |
| *A61K 9/107* | (2006.01) |
| *A23P 10/28* | (2016.01) |
| *A23P 10/35* | (2016.01) |
| *A23P 10/30* | (2016.01) |
| *A23L 33/12* | (2016.01) |
| *A23P 10/20* | (2016.01) |
| *A61K 31/568* | (2006.01) |

(52) U.S. Cl.
CPC ............ *A61K 9/2013* (2013.01); *A23L 33/12* (2016.08); *A23P 10/20* (2016.08); *A23P 10/28* (2016.08); *A23P 10/30* (2016.08); *A23P 10/35* (2016.08); *A61K 9/0053* (2013.01); *A61K 9/1075* (2013.01); *A61K 9/1611* (2013.01); *A61K 9/1623* (2013.01); *A61K 9/1652* (2013.01); *A61K 9/19* (2013.01); *A61K 9/205* (2013.01); *A61K 9/2009* (2013.01); *A61K 9/2054* (2013.01); *A61K 9/2077* (2013.01); *A61K 9/2095* (2013.01); *A61K 9/48* (2013.01); *A61K 9/4808* (2013.01); *A61K 31/337* (2013.01); *A61K 31/568* (2013.01); *A61K 31/58* (2013.01); *A61K 38/12* (2013.01); *A61K 47/14* (2013.01); *A61K 47/44* (2013.01)

(58) Field of Classification Search
CPC .......... A61K 9/19; A61K 9/48; A61K 9/0053; A61K 9/205; A61K 9/1075; A61K 9/1611; A61K 9/1623; A61K 9/1652; A61K 9/2009; A61K 9/2013; A61K 9/2054; A61K 9/2077; A61K 9/2095; A61K 9/4808; A61K 31/58; A61K 31/337; A61K 31/568; A61K 38/12; A61K 47/14; A61K 47/44; A23L 33/12; A23P 10/20; A23P 10/28; A23P 10/30; A23P 10/35; A61P 35/00
See application file for complete search history.

(56) References Cited

U.S. PATENT DOCUMENTS

| | | | |
|---|---|---|---|
| 4,098,802 A | 7/1978 | van der Vies | |
| 5,494,914 A | 2/1996 | Labrie | |
| 5,965,160 A * | 10/1999 | Benita | A61K 9/107 424/455 |
| 6,096,338 A | 8/2000 | Lacy | |
| 6,267,985 B1 | 7/2001 | Chen | |

(Continued)

FOREIGN PATENT DOCUMENTS

| | | |
|---|---|---|
| EP | 2433630 A1 | 3/2012 |
| JP | 2004-534071 A | 11/2004 |

(Continued)

OTHER PUBLICATIONS

Fang et al.: Nanoparticles as delivery carriers for anticancer prodrugs, Expert Opinion on Drug Delivery, 9:6, 657-669, 2012,. Retrieved from internet: https://www.tandfonline.com/doi/pdf/10.1517/17425247.2012.679927.*

(Continued)

*Primary Examiner* — Hong Yu
(74) *Attorney, Agent, or Firm* — Maier & Maier, PLLC

(57) ABSTRACT

The present invention relates to a pharmaceutical composition comprising compound having a log P of at least 5 and a vehicle, wherein the vehicle comprises (a) a fat component in an amount sufficient to achieve lymphatic absorption in a mammal, wherein the fat component is selected from a mono-glyceride of long chain fatty acids, a tri-glyceride of long chain fatty acids, and a mono- and tri-glyceride of long chain fatty acids.

25 Claims, No Drawings

(56) References Cited

U.S. PATENT DOCUMENTS

| | | | |
|---|---|---|---|
| 6,596,306 B1* | 7/2003 | Ho | A61K 9/1075 424/450 |
| 6,977,083 B1 | 12/2005 | Huebler | |
| 6,979,456 B1* | 12/2005 | Parikh | A61K 9/1075 424/422 |
| 7,138,389 B2 | 11/2006 | Amory | |
| 9,682,148 B2* | 6/2017 | Hojgaard | A61K 47/12 |
| 2002/0160049 A1* | 10/2002 | Pather | A61K 9/143 424/489 |
| 2004/0127476 A1 | 7/2004 | Kershman | |
| 2005/0100608 A1 | 5/2005 | Ebert | |
| 2005/0176692 A1 | 8/2005 | Amory | |
| 2005/0209345 A1 | 9/2005 | Charman | |
| 2005/0238673 A1* | 10/2005 | Augustine | A61K 9/1075 424/400 |
| 2005/0287203 A1 | 12/2005 | Nijs Des | |
| 2008/0113031 A1* | 5/2008 | Moodley | A61K 9/5073 424/490 |
| 2008/0305177 A1 | 12/2008 | Kershman | |
| 2008/0317844 A1 | 12/2008 | Dudley | |
| 2009/0075961 A1 | 3/2009 | Ebert | |
| 2010/0136105 A1 | 6/2010 | Chen | |
| 2010/0173882 A1 | 7/2010 | Giliyar | |
| 2011/0039814 A1 | 2/2011 | Huatan | |
| 2011/0251167 A1 | 10/2011 | Dudley | |
| 2012/0322780 A1 | 12/2012 | Giliyar | |
| 2014/0179655 A1 | 6/2014 | Højgaard | |

FOREIGN PATENT DOCUMENTS

| | | |
|---|---|---|
| JP | 2008-504308 A | 2/2008 |
| JP | WO2010/134614 A1 | 11/2012 |
| WO | 200009093 | 2/2000 |
| WO | WO200009093 | 2/2000 |
| WO | 200059482 | 10/2000 |
| WO | WO200059482 | 10/2000 |
| WO | 02/102354 A1 | 12/2002 |
| WO | 2006/000229 A2 | 1/2006 |
| WO | 2011082384 | 7/2011 |
| WO | WO2011082384 | 7/2011 |
| WO | 2011129812 | 10/2011 |
| WO | WO2011129812 | 10/2011 |
| WO | 2012079092 | 6/2012 |
| WO | WO2012079092 | 6/2012 |
| WO | 2014/009434 A1 | 1/2014 |
| WO | 2014096139 | 6/2014 |
| WO | WO2014096139 | 6/2014 |

OTHER PUBLICATIONS

Related U.S. Appl. No. 14/649,687, filed Jun. 4, 2015 (now U.S. Pat. No. 9,682,148), Notice of Allowance, dated Feb. 15, 2017.
Related PCT Appln. No. PCT/EP2015/063606, International Preliminary Report on Patentability, dated Dec. 20, 2016.
Related U.S. Appl. No. 14/649,687 (now U.S. Pat. No. 9,682,148), filed Jun. 4, 2015, Office Action dated Sep. 22, 2016.
Related EP appln. No. 13819021.0, (national phase application of PCT/EP2013/077300), communication dated Jul. 21, 2016.
Related U.S. Appl. No. 14/135,571 (published as US20140179655), filed Jun. 11, 2011, Interview Summary dated Jul. 12, 2016.
Related U.S. Appl. No. 14/649,687 (now U.S. Pat. No. 9,682,148), filed Jun. 4, 2015, Office Action dated Apr. 7, 2016.
Related U.S. Appl. No. 14/135,571 (published as US20140179655), filed Jun. 11, 2011, Office Action dated Feb. 12, 2016.
Related EP appln. No. 13819021.0, (national phase application of PCT/EP2013/077300), amended claims submitted Jan. 18, 2016.
Related PCT Appln. No. PCT/EP2015/063606, International Search Report and Written Opinion, dated Dec. 14, 2015.
Related U.S. Appl. No. 14/135,571 (published as US20140179655), filed Jun. 11, 2011, Interview Summary dated Sep. 18, 2015.
Related U.S. Appl. No. 14/135,571 (published as US20140179655), filed Jun. 11, 2011, Final Office Action dated Jul. 13, 2015.
Related PCT Appln. No. PCT/EP2013/077300 (published as WO2014096139), International Preliminary Report on Patentability, dated Mar. 9, 2015.
Related U.S. Appl. No. 14/135,571 (published as US20140179655), filed Jun. 11, 2011, US Office Action dated Feb. 10, 2015.
Related PCT Appln. No. PCT/EP2013/077300 (published as WO2014096139) response to second written opinion filed Dec. 11, 2014.
Related PCT Appln. No. PCTIEP2013/077300 (published as WO2014096139), 2nd Written Opinion dated Oct. 31, 2014.
Related PCT Appln. No. PCT/EP2013/077300 (published as WO2014096139), Response to 1st Written Opinion dated May 2, 2014.
Related PCT Appln. No. PCT/EP2013/077300 (published as WO2014096139), Search Report and 1st Written Opinion dated Mar. 21, 2014.
Yin et al. Dietary fat modulates the testosterone pharmacokinetics of a new self-emulsifying formulation of oral testosterone undecanoate in hypogonadal men. Journal of Andrology 33; 1282-1290 (2012).
Yin et al. Reexamination of pharmacokinetics of oral testosterone undecanoate in hypogonadal men with a new self-emulsifying formulation. Journal of Andrology 33; 190-201 (2012).
Muchow et al. Production and characterization of testosterone undecanoate-loaded NLC for oral bioavailability enhancement. Drug Development and Industrial Pharmacy 37; 8-14 (2011).
Srinivas-Shankar et al. Review: Testosterone Treatment in Elderly Men. Adv. Ther. 26;25-39 (2009).
White et al. Lymphatic transport of methylnortestosterone undecanoate (MU) and the bioavailability of methylnortestosterone are highly sensitive to the mass of coadministered lipid after oral administration of MU. Journal of Pharmacology and Experimental Therapeutics 331; 700-709 (2009).
Trevaskis et al. Lipid-based delivery systems and intestinal lymphatic drug transport—a mechanistic update. Advanced Drug Delivery Reviews 60; 702-716; (2008).
Page et. al. Nanomilled oral testosterone plus dutasteride effectively normalizes serum testosterone in normal men with induced hypogonadism. Journal of Andrology 29; 222-227 (2008).
Shackleford et al. Lymphatic Absorption of Orally Administered Prodrugs. In Book: Prodrugs, Challenges and Rewards Part 1 and Part 2: 2.5.7; 653-682 (2007).
Porter et al. Lipids and lipid-based formulations: optimizing the oral delivery of lipophilic drugs. Nature Reviews 6; 231-248 (2007).
Schnabel et al. The effect of food composition on serum testosterone levels after oral administration of Andriol Testocaps. Clinical Endocrinology 66; 579-585 (2007).
Amory et al. Oral testosterone in oil: Pharmacokinetic effects of 5a reduction by finasteride or dutasteride and food ntake in man. Journal of Andrology 27; 72-78 (2006).
Amory et al. Oral testosterone in oil plus dutasteride in men: A pharmacokinetic study. The Journal of Clinical Endocrinology & Metabolism 90; 2610-2617 (2005).
Khoo et al. Intestinal lymphatic transport of halofantrine occurs after oral administration of a unit-dose lipid-based formulation to fasted dogs. Pharmaceutical Research 20; 1460-65 (2003).
Woo et al. Enhanced Oral Bioavailability of Paclitaxel by Coadminstrationof the P-Glycoprotein Inhibitor KR30031. Pharmaceutical Res. 20; 24-30 (2003).
Shackleford et al. Contribution of lymphatically transported testosterone undecanoate to the systemic exposure of testosterone after oral administration of two andriol formulations in conscious lymph duct-cannulated dogs. The Journal of Pharmacology and Experimental Therapeutics 306; 925-933 (2003).
Bagchus et al. Important effect of food on the bioavailability of oral testosterone undecanoate. Pharmacotherapy 23;319-325 (2003).
Houwing et al. Pharmacokinetic study in women of three different doses of a new formulation of oral testosterone undecanoate, Andriol Testocaps. Pharmacotherapy 23; 1257-1265 (2003).
Kruijer et al. Improvement of Oral Drug Treatment by Temporary Inhibition of Drug Transporters and/or Cytochrome P450 in the Gastrointestinal Tract and Liver An Overview. The Oncologist 7; 516-530 (2002).

(56) References Cited

OTHER PUBLICATIONS

Porter et al. Intestinal lymphatic drug transport: an update. Advanced Drug Delivery Reviews 50; 61-80 (2001).
Tso et al. Randomized structured triglycerides increase lymphatic absorption of tocopherol and retinol compared with the equivalent physical mixture in a rat model of fat malabsorption. The Journal of Nutrition 131; 2157-2163 (2001).
Gooren a Ten-Year Safety Study of the Oral Androgen Testosterone Undecanoate. Journal of Andrology: 15; 212-215; (1994).
Malcolmson et al. A comparison of the incorporation of model steroids into non-ionic micellar and microemulsion systems. J. Pharm. Pharmacol. 45; 141-143 (1993).
Charman et al. Estimating the maximal potential for intestinal lymphatic transport of lipophilic drug molecules. International Journal of Pharmaceutics 34; 175-178 (1986).
Charman et al. Effects of lipid class and lipid vehicle volume on the intestinal lymphatic transport of DDT. International Journal of Pharmaceutics 33; 165-172 (1986).
Noguchi et al. The effect of drug lipophilicity and lipid vehicles on the lymphatic absorption of various testosterone esters. International Journal of Pharmaceutics 24; 173-184 (1985).
Geere et al. Plasma androgens after a single oral dose of testosterone undecanoate. Archives of Disease in Childhood 55; 218-220 (1980).
Frey et al. Bioavailability of oral testosterone in males. Eur. Clin. Pharmacol. 16; 345-349 (1979).
Horst et al. Lymphatic absorption and metabolism of orally administered testosterone undecanoate in man. Klin. Wschr. 54; 875-879 (1976).
Hirschhäuser et al. Testosterone undecanoate. A new orally active androgen. Acta Endocrinologica 80; 179-187 (1975).
Related US Appln. No. 14135571 (published as US20140179655), filed Jun. 11, 2011, Office Action dated Feb. 12, 2016.
Related US Appln No. 14135571 (published as US20140179655), filed Jun. 11, 2011, Interview Summary dated Sep. 18, 2015.
Related US Appln. No. 14135571 (published as US20140179655), filed Jun. 11, 2011, Final Office Action dated Jul. 13, 2015.
Related US Appln. No. 14135571 (published as US20140179655), filed Jun. 11, 2011, US Office Action dated Feb. 10, 2015.
Related PCT Appln. No. PCT/EP2013/07 300 (published as WO2014096139), Search Report and 1st Written Opinion dated Mar. 21, 2014.
Yin A et al. *Dietary fat modulates the testosterone pharmacokinetics of a new self-emulsifying formulation of oral testosterone undecanoate in hypogonadal men*. Journal of Andrology 33; 1282-1290 (2012).
Yin AY et al. *Reexamination of pharmacokinetics of oral testosterone undecanoate in hypogonadal men with a new self-emulsifying formulation*. Journal of Andrology 33; 190-201 (2012).
Muchow M et al. *Production and characterization of testosterone undecanoate-loaded NLC for oral bioavailability enhancement*. Drug Development and Industrial Pharmacy 37; 8-14 (2011).
Srinivas-Shankar U et al. *Review: Testosterone Treatment in Elderly Men*. Adv. Ther. 26;25-39 (2009).
White KL et al. *Lymphatic transport of methylnortestosterone undecanoate (MU) and the bioavailability of methylnortestosterone are highly sensitive to the mass of coadministered lipid after oral administration of MU*. Journal of Pharmacology and Experimental Therapeutics 331; 700-709 (2009).
Trevaskis NL et al. *Lipid-based delivery systems and intestinal lymphatic drug transport—a mechanistic update*. Advanced Drug Delivery Reviews 60; 702-716; (2008).
Page ST et. al. *Nanomilled oral testosterone plus dutasteride effectively normalizes serum testosterone in normal men with induced hypogonadism*. Journal of Andrology 29; 222-227 (2008).

Shackleford DM et al. *Lymphatic Absorption of Orally Administered Prodrugs*. In Book: Prodrugs, Challenges and Rewards Part 1 and Part 2: 2.5.7; 653-682 (2007).
Porter CJH et al. *Lipids and lipid-based formulations: optimizing the oral delivery of lipophilic drugs*. Nature Reviews 6; 231-248 (2007).
Schnabel PG. et al. *The effect of food composition on serum testosterone levels after oral administration of Andriol Testocaps*. Clinical Endocrinology 66; 579-585 (2007).
Amory JK et al. *Oral testosterone in oil. Pharmacokinetic effects of 5a reduction by finasteride or dutasteride and food intake in man*. Journal of Andrology 27; 72-78 (2006).
Amory JK et al. *Oral testosterone in oil plus dutasteride in men—a pharmacokinetic study*. The Journal of Clinical Endocrinology & Metabolism: 90; 2610-2617 (2005).
Khoo S-M et al. *Intestinal lymphatic transport of halofantrine occurs after oral administration of a unit-dose lipid-based formulation to fasted dogs*. Pharmaceutical. Research 20; 1460-65 (2003).
Woo JS et al. *Enhanced Oral Bioavailability of Paclitaxel by Coadminstrationof the P-Glycoprotein Inhibitor KR30031*. Pharmaceutical Res. 20; 24-30 (2003).
Shackleford DM et al. *Contribution of lymphatically transported testosterone undecanoate to the systemic exposure of testosterone after oral administration of two andriol formulations in conscious lymph duct-cannulated dogs*. The Journal of Pharmacology and Experimental Therapeutics 306; 925-933 (2003).
Bagchus WM et al. *Important effect of food on the bioavailability of oral testosterone undecanoate*. Pharmacotherapy 23; 319-325 (2003).
Houwing NS. et al. *Pharmacokinetic study in women of three different doses of a new formulation of oral testosterone undecanoate, Andriol Testocaps*. Pharmacotherapy 23; 1257-1265 (2003).
Kruijer CMF et al. *Improvement of Oral Drug Treatment by Temporary Inhibition of Drug Transporters and/or Cytochrome P450 in the Gastrointestinal Tract and Liver: An*. The Oncologist 7; 516-530 (2002).
Porter CJH et al. *Intestinal lymphatic drug transport: an update*. Advanced Drug. Delivery Reviews 50; 61-80 (2001).
Tso P et al. *Randomized structured triglycerides increase lymphatic absorption of tocopherol and retinol compared with the equivalent physical mixture in a rat model of fat malabsorption*. The Journal of Nutrition 131; 2157-2163 (2001).
Gooren LJG. *A Ten-Year Safety Study of the Oral Androgen Testosterone Undecanoate*. Journal of Andrology: 15; 212-215; (1994).
Malcolmson C et al. *A comparison of the incorporation of model steroids into non-ionic micellar and microemulsion systems*. J. Pharm. Pharmacol. 45; 141-143 (1993).
Charman WNA et al. *Estimating the maximal potential for intestinal lymphatic transport of lipophilic drug molecules*. International Journal of Pharmaceutics 34; 175-178 (1986).
Charman WNA et al. *Effects of lipid class and lipid vehicle volume on the intestinal lymphatic transport of DDT*. International Journal of Pharmaceutics 33; 165-172 (1986).
Noguchi T et al. *The effect of drug lipophilicity and lipid vehicles on the lymphatic absorption of various testosterone esters*. International Journal of Pharmaceutics 24; 173-184 (1985).
Geere G et al. *Plasma androgens after a single oral dose of testosterone undecanoate*. Archives of Disease in Childhood 55; 218-220 (1980).
Frey H et al. *Bioavailability of oral testosterone in males*. Eur. Clin. Pharmacol. 16; 345-349 (1979).
Horst HJ et al. *Lymphatic absorption and metabolism of orally administered testosterone undecanoate in man*. Klin. Wschr. 54; 875-879 (1976).
Hirschhäuser C et al. *Testosterone undecanoate. A new orally active androgen*. Acta Endocrinologica 80; 179-187 (1975).
Office Action dated Aug. 20, 2019, in corresponding Japanese Application No. 2016-569987; 7 pages.

* cited by examiner

SOLID ORAL DOSAGE FORM OF LIPOPHILIC COMPOUNDS

FIELD OF THE INVENTION

This invention relates to a composition comprising a self-emulsifying drug delivery system capable of delivering and controlling the uptake of compounds having a log P of at least 5 through the lymph and intended for oral use.

The invention provides a mean for controlling the uptake of such compounds improving the absorption and at the same time reducing the variability in the absorption thereby having the advantage that it can be taken both in fed and in fasted state with a reduced or an absence of food effect on the uptake of the compound.

The self-emulsifying drug delivery system can optionally be formulated into a solid oral dosage form further modifying the release thereby leading to a better uptake through the lymph compared to prior oral solid dosage forms of said compounds. The invention provides a composition of a solid oral dosage form containing the self-emulsifying drug delivery system. The self-emulsifying drug delivery system can be included partly in the tablet core to improve the compressibility of said tablet.

The invention relates to pharmaceutical products as well as to dietary supplements.

BACKGROUND OF THE INVENTION

While solid oral dosage forms (granules, tablets or capsules etc.) represent the most convenient and flexible route of administration, it is also a fact that many compounds have very poor and variable oral absorption characteristics. This makes the oral administration of these compounds unsuitable for getting plasma levels high enough to be therapeutically active, or plasma levels stable enough to be within the therapeutic window to maintain therapeutic effect and to avoid toxic peak levels. Absorption problems are normally classified as either due to very low solubility or low permeability. Low solubility causes the compounds to pass through the gastrointestinal tract (GI tract) without being dissolved and therefore not being absorbed. Permeability problems occur, where the compound is soluble, but is not absorbed sufficiently to give any significant blood levels. Such permeability problems can be due to a variety of factors most commonly (1) metabolic instability in the GI tract (2) extensive metabolism when passing the GI barrier (typical CYP metabolism) (3) first pass metabolism from portal vein passing the liver and (4) substrate for the P-glycoprotein (P-gp) efflux pump in the GI tract.

Peptides are an example of a class of molecules that typically show poor oral absorption due to extensive metabolism in the GI tract primarily due to enzymatic degradation in the stomach and upper intestines.

Paclitaxel is another example of compound having permeability issues. Paclitaxel is a taxane used for treatment of oncology indications like breast cancer and ovarian cancer and having a log P of 3.6. Currently Paclitaxel is only available for intravenous infusion due to a very low and variable oral absorption unable to provide therapeutic relevant drug concentrations. Paclitaxel is a molecule with very low solubility (<0.05 mg/ml). CYP3A4 metabolism in the intestine and liver, as well as P-gp mediated efflux activity, are important hindrances for oral absorption of paclitaxel as also described by Kruijer et al. (The Oncologist 7, 516-530, 2002) and Jong Soo Woo et al (Pharm. Res. 20, 24-30, 2003)).

Yet another example is the intravenous drug propofol that due to excessive first pass metabolism has an oral bioavailability of only 3% or lower. Propofol (2,6-diisopropylphenol) is the most extensively used general anesthetic-sedative agent employed today but its use is limited to intravenous dosing necessitating only hospital use. However, Propofol has a long range of pharmacological properties that could be better utilized if an oral dosage form could be made sufficiently bioavailable. Propofol is a potent antioxidant and has been shown to stimulate protein kinase C, inhibit calcium entry in muscle cells and increase the calcium sensitivity of myofilaments in ventricular myocytes. Propofol is also a potent direct vasodilator and bronchodilator and possess anti-inflammatory and antiseizure properties.

The lymphatic path is an alternate pathway to oral absorption by which highly lipophilic compounds can access systemic circulation by uptake in the chylomicrons secreted by the small intestines and thereby be transported in the lymph. In addition this path has the advantage of avoidance of hepatic first-pass metabolism.

Lymphatic absorption is a complex process which is influenced by the formulation as well as by the food taken at the time of dosing. In literature it is described that lipophilic compounds with high log P values can be absorbed into the enterocytes and be incorporated into lipoproteins inside the enterocytes. The compound has to dissolve in the GI-tract and pass the unstirred water layer prior to absorption into the enterocytes. To achieve this, drugs can "hide" in micelles formed either from lipid digestion products and bile or from surfactants present in the formulation.

Fatty acids and monoglycerides are taken up at the same time and re-synthesized to triglycerides, which forms the center of the lipoproteins. Those lipoproteins are then exocytosed from the enterocytes into the lumen and have to diffuse to the lymph. This transport of compound can be increased by increasing the flow of lipoproteins, which again will depend on the amount of lipids in the gut.

As fatty acids and monoglycerides are critical to this absorption mechanism, they have to be supplied either from food or from the formulation of the compound. This can be in the form of fats, triglycerides, monoglycerides or fatty acids. Fats need to be digested to fatty acids and monoglycerides by enzymes in stomach and intestine to be absorbed. Better dispersion to small droplets will help digestion by increasing surface of fat particles giving access for enzymes. In literature different combinations of fats, glycerides or fatty acids have been tested for influence on lymphatic absorption. No general agreements have been reached to which combinations are optimal but from literature it is clear that the fat composition play an important role as well as the amount of fat taken. Khoo et al (Pharm. Res., 20, 1460-1464, 2003) demonstrated that a formulated fat composition of only 600 mg was enough to trigger lipid metabolism in the GI tract and induce high lymphatic absorption of the compound Halofantrine in fasted dogs. Further, the exogenous lipid supplied in the formulaiton was demonstrated to induce transport of endogenous lipid, as a 5-fold flow of lipid was found to be transported to the lymph, compared to the lipid from the formulation.

To be a successful drug candidate in a formulation targeted for lymphatic absorption the compound has to have a log P of at least 5 and a high solubility in lipids. To fulfill these requirements chemical modification of the compound may be required by attachment of a lipophilic moiety to the parent molecule, to increase the lipophilic properties of the compound to an extent that lymphatic transport is possible.

The modified compound is subsequent to absorption converted back to the original compound by enzymatic cleavage either in the blood stream or at the site of action. However, selection of a compound fulfilling these requirements will make it suited for lymphatic absorption but will not necessarily limit the variability in oral bioavailability unless the compound is taken together with a high fat meal.

Testosterone undecanoate is an example of such a compound used for treatment of male hypogonadism. When administered orally testosterone undergoes extensive first pass metabolism both during absorption in the GI tract and in the liver. Testosterone is therefore not available as a marketed oral product. A derivative of testosterone such as testosterone undecanoate has therefore been developed and marketed for oral delivery. Testosterone undecanoate (TU) is a lipophillic ester pro-drug of testosterone having a log P of about 8.7. Testosterone undecanoate is formulated in Castor oil/Propylene glycol monolaurate (293 mg mixture) in a soft gelatin capsule as Andriol® capsules. The lymphatic absorption of TU from this formulations is however shown to be highly dependent upon intake of dietary fat. Therefore this formulation should always be taken with a normal meal to ensure absorption of testosterone undecanoate. As the absorption is extremely dependent on the food intake then absorption becomes very variable and often inadequate. According to the Andriol® label, the oral bioavailability of testosterone undecanoate in a patient in a fed state is more than 50 times that of a fasted state. Due to this food effect, oral testosterone undecanoate is not a suitable therapy for patients who have a low food or low fat intake, such as many elderly patients. Thus, one of the main draw backs of this oral formulation is the variability in absorption and thereby unreliable oral bioavailability and fluctuation in serum levels becoming below the therapeutic level which results in unreliable efficacy.

Abiraterone acetate is used for treatment of metastatic prostate cancer. The API has a low water solubility and a log P of 5.1. The compound has a low permeability resulting in variable absorption. The API is marketed as an oral product Zytiga® to be taken on an empty stomach as the absorption of the API is highly variable and increased upon food intake. Therefore intake of food increases the risk of severe side effects of the drug.

Omega-3 oils such as triglycerides, ethyl esters, free fatty acids and derivatives thereof are used for pharmaceuticals and dietary supplements having a wide spectrum of biological benefits. The omega-3 oils are characterized by having a high Log P value ≥5 and a high solubility in lipids. However, when formulated in capsules such oils often shown an incomplete and variable absorption though a number of different absorption paths within the GI tract.

SUMMARY OF THE INVENTION

The present inventors have realized that a certain fat composition comprising monoglycerides of long chain fatty acids and/or triglycerides of long chain fatty acids can support a compound having a log P of at least 5 so as to achieve lymphatic absorption of the compound in fed as well as in fasted state, and further achieve a high oral bioavailability and at the same time a low variability in absorption.

The present invention relates to a composition, such as a pharmaceutical composition comprising a lipophilic compound having a log P of at least 5 and carrying enough fat in a vehicle to control and achieve lymphatic absorption of the compound in fed as well as in fasted state.

Accordingly, the present invention relates to a pharmaceutical composition comprising compound having a log P of at least 5 and a vehicle, wherein the vehicle comprises (a) a fat component in an amount sufficient to achieve lymphatic absorption in a mammal, wherein the fat component is selected from a mono-glyceride of long chain fatty acids, a tri-glyceride of long chain fatty acids, and a mono- and tri-glyceride of long chain fatty acids.

In a further aspect the present invention relates to a composition comprising a compound having a log P of at least 5 and a vehicle, wherein the vehicle comprises a fat component in an amount sufficient to achieve lymphatic absorption in a mammal, wherein the fat component is selected from a mono-glyceride of long chain fatty acids, a tri-glyceride of long chain fatty acids, and a mono- and tri-glyceride of long chain fatty acids.

In yet a further aspect the present invention relates to a composition comprising a compound having a log P of at least 5 and a vehicle, wherein the vehicle comprises (a) a fat component in an amount sufficient to achieve lymphatic absorption in a mammal, wherein the fat component is selected from a mono-glyceride of long chain fatty acids, a tri-glyceride of long chain fatty acids, and a mono- and tri-glyceride of long chain fatty acids and (b) a tablets core composition suited for optimizing dosing and modifying release of the drug/vehicle system to target the lymph.

In yet another aspect of the present invention relates to a composition comprising a compound having a log P of at least 5, wherein the compound itself comprises (a) a fat component in an amount sufficient to achieve lymphatic absorption in a mammal, wherein the fat component is selected from a mono-glyceride of long chain fatty acids, a tri-glyceride of long chain fatty acids, and a mono- and tri-glyceride of long chain fatty acids and (b) a tablet core composition suited for optimizing dosing and modifying release of the compound/vehicle system to target the lymph.

In a further aspect the present invention relates to a composition comprising a lipophilic compound having a log P of at least 5, and a vehicle, wherein the vehicle comprises (a) a fat component in an amount of at least 500 mg sufficient to achieve lymphatic absorption in a mammal, wherein the fat component is selected from a mono-glyceride of long chain fatty acids, a tri-glyceride of long chain fatty acids, and a mono- and tri-glyceride of long chain fatty acids, wherein the long chain fatty acids in the monoglycerides are selected from fatty acid chains having from 14 to 24 carbon atoms and the long chain fatty acids in the triglycerides are selected from fatty acid chains having from 14 to 24 carbon atoms, and (b) a hydrophilic surfactant wherein the weight ratio (a):(b) is from about 10:1 to about 1:2. Such composition is typically selected from a liquid, a gel, a granule, a capsule or tablet.

In one embodiment the composition is a pharmaceutical composition.

In another embodiment the composition is a dietary composition.

In a further embodiment of the composition the fat component comprises a monoglyceride and a triglyceride of long chain fatty acids, wherein the weight ratio of triglycerides to monoglycerides is in a range from about 2.8:1 to about 1:5.

In a still further embodiment of the composition the fat component is present in an amount sufficient to enhance or promote intestinal lymphatic transport of the compound upon oral administration in the fasted state as well as in fed state, compared to a composition without the fat component.

In a further embodiment of the composition the amount of fat component is from 500 mg to 1200 mg.

In a further embodiment of the composition the amount of fat component is from 500 mg to 10 g. Such as from 1500 mg to 10 g, 2000 mg to 8 g, 3000 mg to 7 g, 4000 mg to 6 g, or from 2000 mg to 6 g.

In a still further embodiment the composition exhibits an AUC(0-inf) (fasted)/AUC(0-inf) (fed)) of at least about 0.4, such as at least about 0.8.

In a further embodiment of the composition the weight ratio of (a):(b) ranges from about 4:1 to about 1:2.

In a still further embodiment of the composition the long chain fatty acids in the monoglycerides are selected from linolenic acid, oleic acid, palmitic acid, linoleic acid, and stearic acid.

In a further embodiment of the composition the long chain fatty acids in the triglycerides are selected from linolenic acid, oleic acid, palmitic acid, linoleic acid, and stearic acid.

In a still further embodiment of the composition the fat component comprising a triglyceride of long chain fatty acids is selected from a naturally derived oil. In one embodiment the naturally derived oil is selected from soybean oil, olive oil, sesame oil, safflower oil, peanut oil, rapeseed oil, sunflower oil, coconut oil, corn oil, sunflower seed oil, cotton seed oil, palm oil, and arachis oil, as well as any combination thereof.

In a further embodiment of the composition the fat component is selected from olive oil, soybean oil, mixtures of olive oil and glycerol mono oleate, and mixtures of soybean oil and glycerol mono oleate. In one embodiment the fat component does not comprise any triglyceride but only monoglyceride, such as glycerol monooleate.

In a still further embodiment of the composition at least about 95% by weight of the lipophilic compound is present in the composition after 2 years of storage at 25° C. and 60% relative humidity.

In a further embodiment of the composition the lipophilic compound is present in an amount from about 0.5% to about 60% by weight, and typically from about 01% to about 30% by weight based on 100% total weight of the composition.

In a still further embodiment of the composition the vehicle is self-emulsifying.

In a further embodiment the composition, upon dilution in purified water, forms droplets with a d50 of less than about 200 micrometer. In one embodiment the droplets have a d50 of less than about 150 micrometer, such as less than about 100 micrometer, such as less than about 40 micrometer, less than about 20 micrometer, less than about 10 micrometer, or less than about 5 micrometer.

In a still further embodiment of the composition the lipophilic compound is in a solid core, such as a tablet core. In one embodiment the vehicle is adsorbed into the solid core. In a further embodiment the vehicle is adsorbed into the tablet core. In another embodiment the lipophilic compound is dissolved in the vehicle and adsorbed into the solid core. In a still further embodiment the lipophilic compound is dissolved in the vehicle and adsorbed into the tablet core.

In a further embodiment the composition is a tablet having a solid core comprising the lipophilic compound having a log P of at least 5, and the vehicle absorbed into the solid core, wherein the vehicle comprises (a) a fat component in an amount of at least 500 mg sufficient to achieve lymphatic absorption in a mammal, wherein the fat component is selected from a mono-glyceride of long chain fatty acids, a tri-glyceride of long chain fatty acids, and a mono- and tri-glyceride of long chain fatty acids, wherein the long chain fatty acids in the monoglycerides are selected from fatty acid chains having from 14 to 24 carbon atoms and the long chain fatty acids in the triglycerides are selected from fatty acid chains having from 14 to 24 carbon atoms, and (b) a hydrophilic surfactant wherein the weight ratio (a):(b) is from about 10:1 to about 1:2; wherein the fat component is present in an amount sufficient to enhance or promote intestinal lymphatic transport of the compound upon oral administration in the fasted state as well as in fed state, compared to a composition without the vehicle component in said solid core. In one embodiment the lipophilic compound is dissolved in the vehicle and adsorbed into the solid core. In another embodiment the lipophilic compound is partly or fully formulated into the solid core and then the vehicle is adsorbed into the solid core.

In a still further embodiment of the composition the solid core has a porosity of at least 30% volume, such as at least 40%, such as at least 50%, such as at least 55%, such as at least 60%, for instance form 30% volume to 60% volume, or from 40% volume to 55% volume. Examples of such solid cores with high porosity are described in for instance European Patent application EP1765297.

A particular useful composition is a solid core, wherein the solid core comprises a silicon dioxide in an amount of at least 40% by weight of the total composition without the lipophilic compound.

When the composition is selected from a solid core, such core is typically a compressed or molded tablet core having a hardness of from 20N to 150N.

In a further embodiment of the composition the hydrophilic surfactant is selected from a hydrophilic surfactant with a Hydrophile-Lipophile Balance (HLB) value of 10 or higher. Typically, the hydrophilic surfactant is selected from hydrogenated castor oil ethoxylates, polysorbates and any combination thereof.

In a still further embodiment of the composition the lipophilic compound is selected from abiraterone acetate, acitretin, allylestrenol, alpha tocopherol, amidarone, aprepitant, atorvastatin, bexarotene, bromocriptine, candesartan, cinacalcet, clomiphene, diethyl stilbestrol, dihomo-gamma-linoleic acid, ebastine, ergocalciferol, fenofibrate, fucidic acid, halofantrine, irbesartan, isotretinoin, itraconazole, lapatinib, liraglutide, loratidine, nandrolone decanoate, nelfinavir, olmesartan, orlistat, posaconazole, probucol, raloxifene, ritonavir, tamoxifen, telmisartan, teprenone, tipranavir, valsartan, and zuclopenthixol. Each of these compounds constitute individual embodiments and may be elected as the specific lipophilic compound in any of the above embodiments and aspects of the present invention, such as for instance, abiraterone acetate.

In a further embodiment of the composition the lipophilic compound is selected from a compound which has been modified by attachment of a lipophilic moiety to increase the lipophilicity of the lipophilic compound to at least log P of at least 5 making it suitable for lymphatic uptake. Typically, the compound is a pro-drug, such as an ester or amide. Examples of such pro-drugs are selected from paclitaxel docosahexaenoate, paclitaxel undecanoate, paclitaxel oleate and paclitaxel stearate; octreotide covalently attached to a fatty acid with at least 20 carbon atoms in an amide formation; leuprolide covalently attached to a fatty acid ester via the aliphatic or aromatic hydroxyl group present in the peptide; propofol covalently attached to a fatty acid ester via the phenolic aromatic hydroxy group; and testosterone undecanoate. Each of these modified compounds constitute individual embodiments and may be elected as the specific lipophilic compound in any of the above embodiments and aspects of the present invention, such as for instance, paclitaxel docosahexaenoate.

In a special embodiment the present invention relates to a composition comprising abiraterone acetate, and a vehicle, wherein the vehicle comprises (a) a fat component in an amount of at least 500 mg sufficient to achieve lymphatic absorption in a mammal, wherein the fat component is selected from a mono-glyceride of long chain fatty acids, a tri-glyceride of long chain fatty acids, and a mono- and tri-glyceride of long chain fatty acids, wherein the long chain fatty acids in the monoglycerides are selected from fatty acid chains having from 14 to 24 carbon atoms and the long chain fatty acids in the triglycerides are selected from fatty acid chains having from 14 to 24 carbon atoms, and (b) a hydrophilic surfactant wherein the weight ratio (a):(b) is from about 10:1 to about 1:2, for use in the treatment of cancer, such as prostate cancer, e.g. castration-resistant prostate cancer.

In another special embodiment the present invention relates to a composition comprising a paclitaxel prodrug, such as paclitaxel docosahexaenoate, paclitaxel undecanoate, paclitaxel oleate and paclitaxel stearate, and a vehicle, wherein the vehicle comprises (a) a fat component in an amount of at least 500 mg sufficient to achieve lymphatic absorption in a mammal, wherein the fat component is selected from a mono-glyceride of long chain fatty acids, a tri-glyceride of long chain fatty acids, and a mono- and tri-glyceride of long chain fatty acids, wherein the long chain fatty acids in the monoglycerides are selected from fatty acid chains having from 14 to 24 carbon atoms and the long chain fatty acids in the triglycerides are selected from fatty acid chains having from 14 to 24 carbon atoms, and (b) a hydrophilic surfactant wherein the weight ratio (a):(b) is from about 10:1 to about 1:2, for use in the treatment of cancer, such as breast cancer, ovarian cancer, non-small cell lung cancer (NSCLC) and prostate cancer.

In a still further aspect the present invention relates to a method for treatment of cancer in a mammal, such as a human, comprising administering a composition comprising a paclitaxel prodrug, such as paclitaxel docosahexaenoate, paclitaxel undecanoate, paclitaxel oleate and paclitaxel stearate, and a vehicle, wherein the vehicle comprises (a) a fat component in an amount of at least 500 mg sufficient to achieve lymphatic absorption in a mammal, wherein the fat component is selected from a mono-glyceride of long chain fatty acids, a tri-glyceride of long chain fatty acids, and a mono- and tri-glyceride of long chain fatty acids, wherein the long chain fatty acids in the monoglycerides are selected from fatty acid chains having from 14 to 24 carbon atoms and the long chain fatty acids in the triglycerides are selected from fatty acid chains having from 14 to 24 carbon atoms, and (b) a hydrophilic surfactant wherein the weight ratio (a):(b) is from about 10:1 to about 1:2, wherein the composition is effective to treat said cancer.

In a further aspect the present invention relates to a method for treatment of cancer in a mammal, such as a human, comprising administering a composition comprising abiraterone acetate, and a vehicle, wherein the vehicle comprises (a) a fat component in an amount of at least 500 mg sufficient to achieve lymphatic absorption in a mammal, wherein the fat component is selected from a mono-glyceride of long chain fatty acids, a tri-glyceride of long chain fatty acids, and a mono- and tri-glyceride of long chain fatty acids, wherein the long chain fatty acids in the monoglycerides are selected from fatty acid chains having from 14 to 24 carbon atoms and the long chain fatty acids in the triglycerides are selected from fatty acid chains having from 14 to 24 carbon atoms, and (b) a hydrophilic surfactant wherein the weight ratio (a):(b) is from about 10:1 to about 1:2, wherein the composition is effective to treat said cancer.

In a still further aspect the present invention relates to a composition comprising an omega-3 oil and/or an omega-6 oil, and a vehicle, wherein the vehicle comprises (a) a fat component in an amount of at least 500 mg sufficient to achieve lymphatic absorption in a mammal, wherein the fat component is selected from a mono-glyceride of long chain fatty acids, a tri-glyceride of long chain fatty acids, and a mono- and tri-glyceride of long chain fatty acids, wherein the long chain fatty acids in the monoglycerides are selected from fatty acid chains having from 14 to 24 carbon atoms and the long chain fatty acids in the triglycerides are selected from fatty acid chains having from 14 to 24 carbon atoms, and (b) a hydrophilic surfactant wherein the weight ratio (a):(b) is from about 10:1 to about 1:2. In one embodiment the omega-3 oil and/or the omega-6 oil is selected from an omega-3 oil. In another embodiment the omega-3 oil and/or the omega-6 oil is selected from an omega-6 oil. In yet another embodiment the omega-3 oil and/or the omega-6 oil is selected from a mixture of an omega-3 oil and an omega-6 oil. Further embodiments may be elected from any of the above described embodiments in connection with the above aspects of a composition comprising a lipophilic compound having a log P of at least 5 and embodiments thereof as understood by the skilled person.

In a further aspect the present invention relates to a tablet comprising (i) a solid core and (ii) a composition comprising an omega-3 oil and a vehicle, wherein the vehicle comprises (a) a fat component in an amount of at least 500 mg sufficient to achieve lymphatic absorption in a mammal, wherein the fat component is selected from a mono-glyceride of long chain fatty acids, a tri-glyceride of long chain fatty acids, and a mono- and tri-glyceride of long chain fatty acids, wherein the long chain fatty acids in the monoglycerides are selected from fatty acid chains having from 14 to 24 carbon atoms and the long chain fatty acids in the triglycerides are selected from fatty acid chains having from 14 to 24 carbon atoms, and (b) a hydrophilic surfactant wherein the weight ratio (a):(b) is from about 10:1 to about 1:2; wherein the solid core comprises a silicon dioxide and wherein the composition comprising the omega-3 oil and the vehicle is adsorbed into the solid core. Further embodiments may be elected from any of the above described embodiments in connection with the above aspects of a composition comprising a lipophilic compound having a log P of at least 5 and embodiments thereof as understood by the skilled person.

In a further aspect the present invention relates to a tablet comprising (i) a solid core and (ii) a composition comprising an omega-3 oil and a vehicle comprising a hydrophilic surfactant; wherein the solid core comprises a silicon dioxide and wherein the composition comprising the omega-3 oil and the vehicle is adsorbed into the solid core. Further embodiments may be elected from any of the above described embodiments in connection with the above aspects of a composition comprising a lipophilic compound having a log P of at least 5 and embodiments thereof as understood by the skilled person. In another embodiment the weight ratio of omega-3 oil:surfactant ranges from about 3:2 to about 10:1.

In a still further aspect the present invention relates to a tablet comprising a solid core and an omega-3 oil, wherein the solid core comprises silicon dioxide and wherein the omega-3 oil is adsorbed into the solid core. In one embodiment the solid core has a porosity of at least 30% volume, such as at least 40%, such as at least 50%, such as at least 55%, such as at least 60%, for instance form 30% volume to 60% volume, or from 40% volume to 55% volume. In a particular useful tablet the silicon dioxide is present in an amount of at least 40% by weight of the total composition without the omega-3 oil.

In a further embodiment of the tablet comprising a solid core, the solid core enhance or promote intestinal lymphatic transport of the omega-3-oil upon oral administration in the fasted state as well as in fed state, compared to a composition or omega-3 oil not adsorbed into said solid core. In one embodiment the omega-3 oil is present in an amount from about 0.5% to about 80% and typically from about 30 to about 60% by weight based on 100% total weight of the solid core.

In a further aspect the present invention relates to a tablet comprising a solid core, wherein the solid core comprises a silicon dioxide and an appropriate excipient to improve the poor compressibility of silicon dioxide to be able to produce high-level silicon dioxide tablets without cracking and capping. Preferably, the appropriate excipient is selected from Hypromellose 100 cps, maltodextrin, and low-substituted Hydroxypropyl cellulose. In one embodiment the tablet is empty of any liquid composition and any pharmaceutical compound, or omega-3 oil. In another embodiment the solid core has a porosity of at least 30% volume, such as at least 40%, such as at least 50%, such as at least 55%, such as at least 60%, for instance form 30% volume to 60% volume, or from 40% volume to 55% volume. In a further embodiment the solid core further comprises an antioxidant, such as without limitation alpha-Tocopeherol, gamma-Tocopherol, ascorbyl palmitate, ascorbic acid, Butylated Hydroxytoluene, Butylated Hydroxyanisole, citric acid or propyl gallate.

Further objects and advantages of the present invention will appear from the following description, and claims.

DESCRIPTION OF THE INVENTION

It is speculated whether effective lymphatic absorption of lipophilic compounds with high log P and high solubility in triglycerides can be achieved with low amounts of lipid relevant for single dose formulations.

Improving the lymphatic absorption of lipophilic compounds can be accomplished in two ways.

Solubilization of fat components into micelles can be achieved by proper selection of surfactants. Solubilization will improve both the rate of digestion of fat and the amount of fat and the lipophilic compound transported over the unstirred water layer. Solubilization of lipophilic compound and formulation is part of the technology concept of the present invention.

Further, the proper selection of fat components which trigger lipid metabolism in the GI tract and induce release of the lipophilic compound into the lymphatic system is part of the technology concept of the present invention. The contrast between the reported data from Khoo et al (Pharm. Res., 20, 1460-1464, 2003) and Schnabel et al (Clin Endocrin. 66, 579-585, 2007) have made the present inventors realize that both fat composition and amount of fat are important parameters if the system shall control the lymphatic uptake. The amount of fat is an issue especially if the lipophilic compound is taken in fasted state, and if the fat composition is not optimal or the amount is too low, variation in absorption will be the expected result.

It is most likely that an efficient formulation based on incorporation of larger amount of selected solubilizers and fats will result in an increase in bioavailability and/or decrease in variability compared to current formulations of a lipophilic compound. Further, having the formulation to control the lymphatic uptake will obviate the requirement for simultaneous food intake.

The present invention relates to a composition comprising a compound having a log P of at least 5 and a vehicle, wherein the vehicle comprises (a) a fat component in an amount sufficient to control and achieve lymphatic absorption in a mammal, wherein the fat component is selected from a mono-glyceride of long chain fatty acids, a tri-glyceride of long chain fatty acids, and a mono- and tri-glyceride of long chain fatty acids.

Examples of compounds with a log P of at least 5 that may be suitable for formulation according to the present invention include but is not limited to the following:

Abiraterone acetate, acitretin, allylestrenol, alpha tocopherol, amidarone, aprepitant, atorvastatin, bexarotene, bromocriptine, candesartan, cinacalcet, clomiphene, diethyl stilbestrol, dihomo-gamma-linoleic acid, ebastine, ergocalciferol, fenofibrate, fucidic acid, halofantrine, irbesartan, isotretinoin, itraconazole, lapatinib, liraglutide, loratidine, nandrolone decanoate, nelfinavir, olmesartan, orlistat, posaconazole, probucol, raloxifene, ritonavir, tacrolimus, tamoxifen, telmisartan, teprenone, tipranavir, valsartan, zuclopenthixol.

The lipophilic compound may be in free acid, free base or salt form, and mixtures of lipophilic compounds may be used where therapeutically effective.

In another embodiment the invention relates to a composition comprising a compound which has to be modified e.g. by attachment of a lipophilic moiety to increase the lipophilicity of the compound to at least log P of at least 5 making it suitable for lymphatic uptake. Such lipophilic moiety can be in the form of an ester or an amide. Subsequent absorption the binding of the moiety is cleaved by endogenous peptidases or hydrolysed by hydroxylases thereby liberating the active molecule in the blood stream or at the site of therapeutic action. The composition further comprises a vehicle, wherein the vehicle comprises (a) a fat component in an amount sufficient to control and achieve lymphatic absorption in a mammal, wherein the fat component is selected from a mono-glyceride of long chain fatty acids, a tri-glyceride of long chain fatty acids, and a mono- and tri-glyceride of long chain fatty acids.

Paclitaxel is an example of a compound having a log P less than 5 that can be esterified to gain a lipophilicity high enough for lymphatic absorption in said composition. Examples of such esters are without limitation docosahexaenoate, undecanoate, oleate and stearate.

Propofol is another example of a compound that can be esterified to a fatty acid ester, such as without limitation propofol-acetate, propofol-undecanoate, propofol palmitate, propofol oleate, propofol-docosahexexoate and propofol-eicosapentanoate.

Testosterone is an example of another compound having a log P less than 5 that can be esterified to gain a lipophilicity high enough for lymphatic absorption in said composition. Examples of such esters without limitation are undecanoate, palmitate and oleate.

Yet another group of compounds which has to be modified is the peptides that can be lipophilic modified with an ester or an amide. The size and length of the lipophilic moiety attached to the peptide can be varied to gain sufficient lipophilicity of said compound. Octreotide is an example of a relative hydrophilic small peptide having a log P around 1. By attachment of a fatty acid with at least 20 carbon atoms in an amide formation, a compound with a log P of at least 5 is obtained. Another example is the nonapeptide leuprolide having a log P of about 3 where a fatty acid ester can be formed on the aliphatic or aromatic hydroxyl group present in the peptide providing a log P of at least 5.

In yet another embodiment of the invention the composition comprises a compound being an omega-3 or an omega-6 oil or a mixture thereof such as triglycerides, free omega-3-fatty acids, omega-3-fatty acids ethyl esters, salts or derivatives thereof having a log P of at least 5. The composition further comprise a vehicle, wherein the vehicle comprises (a) a fat component in an amount sufficient to control and achieve lymphatic absorption in a mammal, wherein the fat component is selected from a mono-glyceride of long chain fatty acids, a tri-glyceride of long chain fatty acids, and a mono- and tri-glyceride of long chain fatty acids.

Examples of omega-3-fatty acids are but not limited to alpha-linolenic acid (ALA), eicosapentaenoic acid (EPA), docosahexaenoic acid (DHA and an example of an omega-6 fatty acid is gamma-linolenic acid (GLA). Examples of omega-3 fatty acid ethyl esters are but not limited to EPA ethyl ester: (all-Z)-5,8,11,14,17-Eicosapentaenoic acid ethyl ester and DHA ethyl ester: (all-Z)-4,7,10,13,16,19-Docosahexaenoic acid ethyl ester. Each of these omega-3 oils constitute individual embodiments and may be elected as the specific lipophilic compound or omega-3 oil in any of the above embodiments and aspects of the present invention, such as for instance, ALA. Each of these omega-6 oils constitute individual embodiments and may be elected as the specific lipophilic compound or omega-6 oil in any of the above embodiments and aspects of the present invention, such as for instance, GLA.

In an embodiment the vehicle further comprises (b) a hydrophilic surfactant, wherein the weight ratio (a):(b) is from about 10:1 to about 1:2, such as from about 4:1 to about 1:2. The weight ratio (a):(b) may range from about 40:60 to about 80:20, such as from about 50:50 to about 70:30. In one embodiment, the ratio (a):(b) ranges from about 55:45 to about 65:35, such as about 60:40.

The hydrophilic surfactant may be any described herein. Suitable hydrophilic surfactants include hydrogenated castor oil ethoxylates (such as Polyoxyl 35 castor oil), polysorbates (such as polysorbate 80) or any other hydrophilic surfactant with a Hydrophile-Lipophile Balance (HLB) value of 10 or higher, and any combination of any of the foregoing.

In another embodiment the fat component further comprises a triglyceride of long chain fatty acids, wherein the weight ratio of triglycerides to monoglycerides is in a range from about 2.8:1 to about 1:5. When one or more triglycerides are present in the fat component, the ratio of triglyceride to monoglyceride may, for instance, range from about 2:1 to about 1:5, such as from about 3:2 to about 1:4. In one embodiment, the ratio is from about 1:1 to about 1:3.

In a further embodiment the fat component is present in an amount sufficient to enhance or promote intestinal lymphatic transport of the lipophilic compound upon oral administration in the fasted state as well as in fed state, compared to a composition without the fat component.

In a further embodiment the amount of fat component is at least about 500 mg, such as at least 600 mg, at least 700 mg, at least 800 mg, at least 1000 mg, such as from about 500 mg to about 1000 mg.

In a further embodiment of the composition the amount of fat component is from 500 mg to 10 g. Such as from 1500 mg to 10 g, 2000 mg to 8 g, 3000 mg to 7 g, 4000 mg to 6 g, or from 2000 mg to 6 g.

It is known to the person skilled in the art that high amounts of fat may have to be administered in more than one composition, which makes it clear that for instance 2400 mg fat may preferably be administered as 6 dosages of 400 mg fat each, or as 3 dosages of 800 mg each. Therefore a composition of the present invention is intended to mean one or more compositions comprising, typically, at least 500 mg fat in total, for instance 5 capsules containing 100 mg fat each or e.g. 6 capsules comprising 400 mg fat each.

In a still further embodiment the composition exhibits an $AUC_{(0-inf)(fasted)}/AUC_{(0-inf)(fed)}$ of at least about 0.4. The present composition exhibits enhanced bioavailability and a reduced food effect. Without being bound by or limited to theory, it is believed that the formulation achieves this result by controlling and enhancing absorption of the lipophilic compound by the intestinal lymphatic system rather than by way of portal circulation. In a preferred embodiment, the formulation exhibits an $AUC_{0-inf(fasted)}/AUC_{0-inf(fed)}$ (i.e., $AUC_{(0-inf)(fasted)}/AUC_{(0-inf)(fed)}$) of at least about 0.4. In further preferred embodiments, the formulation exhibits an AUC0-inf (fasted)/AUC0-inf (fed) of at least about 0.6, at least about 0.7, or at least about 0.8.

The long chain fatty acids in the monoglycerides and triglycerides may have range in length from 14 to 24 carbon atoms.

In a further embodiment the long chain fatty acids in the monoglycerides are selected from fatty acid chains having from 14 to 24 carbon atoms, such as from 16 to 20 carbon atoms.

In a still further embodiment the long chain fatty acids in the triglycerides are selected from fatty acid chains having from 14 to 24 carbon atoms, such as from 16 to 20 carbon atoms.

Suitable fatty acids for the monoglycerides and triglycerides include, but are not limited to, (A) linoleic acid (18:2), (B) oleic acid (18:1), (C) palmitic acid (16), (D) linoleic acid (18:3), and (E) stearic (18:0). (The first number in the parentheticals in the prior sentence refers to the number of carbon atoms in the fatty acid chain, and the second number refers to the degree of unsaturation (e.g., 1 refers to 1 double bond).).

When triglycerides are present in the fat component they may typically be present as oils. In a further embodiment the fat component comprising a triglyceride of long chain fatty acids is selected from an oil such as soybean oil, olive oil, sesame oil, safflower oil, or any combination thereof.

Sometimes the fat component does not comprise any triglyceride but only monoglyceride such as glycerol monooleate.

In another embodiment, the fat component comprises monoglycerides and triglycerides.

In a further embodiment, the fat component is selected from olive oil.

In a still further embodiment, the fat component is selected from soybean oil.

In a still further embodiment, the fat component is selected from omega 3 oil.

In a further embodiment, the fat component is selected from a mixture of olive oil and glycerol mono oleate.

In a still further embodiment, the fat component is selected from a mixture of soybean oil and glycerol mono oleate.

In a still further embodiment, the fat component is selected from omega 3 oil and glycerol mono oleate.

The vehicle formulation may be a liquid and it may also be self-emulsifying when introduced to aqueous media. In a certain embodiment, the composition, upon dilution in purified water, forms droplets with a $d_{50}$ of less than about 50 µm. In a further embodiment the composition, upon dilution in purified water, forms droplets with a $d_{50}$ of less than about 200 micrometres, such as less than about 150 micrometres, such as less than about 100 micrometres, such as less than about 40 micrometres, such as less than about 20 micrometres, less than about 10 micrometres, or less than about 5 micrometres, such as droplets having a $d_{50}$ ranging from about 0.01 to about 200 µm, such as from about 0.1 to about 40 µm.

In a further embodiment the lipophilic compound is in a solid core, such as a tablet core.

In a still further embodiment the vehicle is adsorbed into the solid core. When the composition is in the form of a tablet, the lipophilic compound can optionally be dissolved in the vehicle or the lipophilic compound can optionally be fully or partly included in the tablet core before adsorbing of the vehicle. In an embodiment the lipophilic compound is dissolved in the vehicle and adsorbed into the solid core.

When the dosage form is solid it may be a compressed or molded tablet having a hardness of from about 20 N to about 150 N.

In a further embodiment the lipophilic compound (having a log p of at least 5) is a pro-drug, such as an ester or an amide.

The composition of the present invention may be selected from a liquid, a gel, a granule, a capsule or a tablet. In one embodiment, the composition, e.g. oral, could be a liquid. In such case the lipophilic compound is solubilized in the vehicle. In another embodiment, the composition, e.g. oral, is a capsule, and in this case the lipophilic compound is solubilized in the vehicle and is filled into soft or hard capsules.

In a further aspect the present invention relates to an oral dosage form, such as a solid oral dosage form, comprising the pharmaceutical composition of the invention. The composition may be incorporated into a solid oral dosage form having a sorbent as discussed below. The compound can be solubilized in the vehicle or it can be fully or partly added to the composition before compression it into a tablet.

Furthermore, the absorption to a solid core, such as a tablet core, can be beneficial in delaying the release of the SEED system within the gastrointestinal tract. When the self-emulsifying drug delivery system is formulated in a capsule the self-emulsifying drug delivery system is typically released immediately after oral intake, whereas when the self-emulsifying drug delivery system is absorbed in a tablet core, the dissolution of the self-emulsifying drug delivery system is modified and delayed somewhat. This effect can be observed when comparing the dissolution profiles of a self-emulsifying drug delivery system from either a capsule or the tablet. Surprisingly, the tablet reduces the release rate of the self-emulsifying drug delivery system also help in decreasing the variability in absorption, thus help the absorption profile further to be nearly independent of food intake. This is an especially important and useful property for compounds having a narrow therapeutic window.

The benefit of having the tablet core as the dosage form, has also been shown even without the active compound initially being dissolved in a self-emulsifying drug delivery system. This is especially useful when the compound is a liquid and a high load of the compound is needed in the dosage form and especially such as for omega 3 fatty acids, triglycerides, ethyl esters and derivatives thereof where higher absorption and lower variability and elimination of fish taste or burbs can be achieved by dosing the oil when absorbed in the tablet compared to when it is dosed as a conventional capsule.

Yet another embodiment is an oral tablet comprising (i) an adsorbent excipient, (ii) optionally a binder or release enhancing agent, (iii) optionally a disintegrant or other standard tablet excipients, (iv) a composition of the present invention.

The solid oral dosage form may be prepared by preparing a granulate of the adsorbant excipient and optionally (a) binder(s) and preparing a tablet comprising an adsorbent excipient, optionally a binder, optionally a release enhancing agent, optionally a disintegrant and optionally other normal tablet excipients (binders, lubricants, flow enhancers etc), and adsorbing the mixture of a compound in the vehicle into the tablets, until the lipophilic compound is adsorbed, for example, to about 50% or more (e.g., 70% or more) of the adsorbing capacity.

The adsorbtion may be performed by placing the tablet in an excess amount of the lipophilic compound in the vehicle for a sufficient amount of time. In an embodiment, the adsorbing is performed under pressure. The time period of adsorbing the compound may be from about 15 minutes to about 10 hours.

Yet another embodiment is a method of delivering a compound to the systemic circulation through the lymphatic transport system by the oral administration to a mammal subject of a solid oral dosage form or oral pharmaceutical formulation of the present invention.

Preferably, the solid oral dosage form includes at least about 300 mg (e.g., at least about 400 mg, at least about 500 mg, at least about 550 mg, or at least about 600 mg) of the long chain lipids that is a mono-glyceride of long chain fatty acids, a tri-glyceride of long chain fatty acids, or a mono- and tri-glyceride of long chain fatty acids.

In a further embodiment, the total content of long chain lipids in the solid oral dosage form ranges from about 600 to about 800 mg, such as from about 600 to about 700 mg.

A typical embodiment of the solid oral dosage form comprises (A) a solid carrier comprising adsorbent Silicon dioxide; and (B) a mixture comprising the lipophilic compound in a vehicle comprising (a) a fat component in an amount sufficient to achieve lymphatic absorption in a mammal, wherein the fat component comprises a monoglyceride of long chain fatty acids, and (ii) optionally, one or more hydrophilic surfactants, wherein (ai) the mixture is adsorbed in the porous silicon dioxide, and (bi) the solid oral dosage form comprises from about 600 to about 1000 mg of long chain lipids (e.g., from about 600 to about 800 mg).

As explained herein the pharmaceutical composition of the present invention may be administered so as to avoid the requirement of orally administering a compound in the fed state.

In a further aspect the present invention relates to a method of preparing the composition of the invention comprising formulating the lipophilic compound with a vehicle wherein the vehicle comprises (a) a fat component in an amount of at least 500 mg sufficient to achieve lymphatic absorption in a mammal, wherein the fat component is selected from a mono-glyceride of long chain fatty acids, a tri-glyceride of long chain fatty acids, and a mono- and tri-glyceride of long chain fatty acids, wherein the long chain fatty acids in the monoglycerides are selected from fatty acid chains having from 14 to 24 carbon atoms and the long chain fatty acids in the triglycerides are selected from fatty acid chains having from 14 to 24 carbon atoms, and (b) a hydrophilic surfactant wherein the weight ratio (a):(b) is from about 10:1 to about 1:2, such that oral administration of the composition in the fed or fasted state facilitates delivery of the compound to the systemic circulation through the lymphatic transport system.

The solid oral dosage form of the present invention can provide a number of advantages over conventional methods for the delivery of a compound within the subject. For example, the solid oral dosage forms comprising the composition of the present invention can provide sufficient oral bioavailability of the lipophilic compound and at the same time a low variability in absorption regardless of whether the subject is in the fed or fasted state. Accordingly, in the methods of treatment described, the solid oral dosage forms may be administered in both the fed or fasted state.

This is a particular advantage when administering narrow therapeutic indexed drugs (lipophilic compounds) where variability in absorption due to food could provide either a risk of severe side-effects or insufficient drug levels. This is also an advantage when treating an elderly population, who typically does not eat a sufficient amount of fat to achieve satisfactory absorption of a drug which is dependent upon food intake to be absorbed.

The solid oral dosage forms of the present invention may substantially avoid passage of the compound to the liver via the portal blood.

This is an advantages for compound undergoing extensive metabolism when passing the GI tract barrier or being substrates for the P-GP efflux pump and therefore not being absorbed through the portal vein in sufficient amount to achieve therapeutic drug levels or for drugs having a high first pass metabolism making sufficient absorption impossible.

The formulation in the form of a tablet may have several advantages, including reduced food effect, the possibility of including functional coatings, oxygen protection, targeted release, use of excipients which are not compatible with capsules, simpler production process, and use of standard equipment.

Compound

The lipophilic compound may be either a pro-drug or a salt of the drug as explained above. The compound should have a log P of at least 5.

As explained above the compound may be solubilized in the vehicle before adsorbing into the solid adsorbent of the solid oral dosage form or the compound may be solubilized in the vehicle before filling into a capsule.

In a typical embodiment the oral dosage form includes the compound as partly or fully incorporated into a tablet core together with an adsorbent and the vehicle is adsorbed into this tablet core to create the solid oral dosage form. The vehicle adsorbed can either be without or having some of the compound solubilized.

In yet another embodiment the compound itself is without being solubilized in the vehicle adsorbed into the solid oral dosage form. This is especially useful when the API (lipophilic compound) is a liquid and a high drug load is needed in the dosage form and especially for compounds such as for omega 3 fatty acids, triglycerides, ethyl esters and derivatives thereof where higher absorption and lower variability and elimination of fish taste and burbs can be achieved by dosing the oil absorbed in a tablet compared to when it is dosed as a conventional capsule.

The Vehicle

The vehicle may be composed from lipids (mono- and/or triglycerides) and optionally hydrophilic surfactants as explained herein.

By lipids is understood to refer to, if not indicated otherwise, saturated, mono-unsaturated and polyunsaturated fatty acids and derivatives thereof. Derivatives include esters such as mono-, di- and triglycerides, as well as phospholipids or other glyceride esters.

The lipids may be composed of long chain fatty acids of from $C_{14}$ to $C_{24}$ or a derivative thereof, indicating from 14 carbon atoms in the fatty acid chain up to 24 carbon atoms in the fatty acid chain. The fatty acid may be a saturated, monounsaturated or polyunsaturated fatty acid or a derivative thereof. Each chain in the fatty acid or glyceride may have, for example, 0, 1, 2, or 3 double bonds. The term "long chain lipid" refers to long chain (i.e., $C_{14}$ or greater, such as $C_{14}$-$C_{24}$ or $C_{16}$-$C_{18}$) fatty acids, as well as derivatives of long chain fatty acids. Examples of suitable lipids for the vehicle include those which stimulate the production of endogenous lipid such as those described in U.S. Pat. No. 6,096,338, the entire contents of which is incorporated herein by reference.

The lipids may be formulated with the lipophilic compound in the form of a naturally derived oil, such as soybean oil, olive oil, peanut oil, rapeseed oil, sunflower oil, coconut oil, corn oil, sunflower seed oil, cotton seed oil, palm oil, arachis oil, safflower oil, omega 3 oils or a combination thereof. Other suitable lipids include, but are not limited to, mono and di glycerides of the aforementioned oils, glycerol monooleate, glyceryl monolinoleate, and any combination of any of the foregoing.

The lipid(s) may be used alone or in combination with one or more. In one embodiment, the lipids alone or in combination with a surfactant stimulate the production of endogenous lipid or otherwise enhance or promote lymphatic transport of the drug or drug derivative. For instance, the vehicle may be selected from long chain lipids, and long chain lipids in combination with a hydrophilic surfactant.

Examples of surfactants which may be suitable include esters of mono or di-glycerides, (such as the acetic, succinic, lactic, citric or tartaric esters), propylene glycol, mono or di-esters of fatty acids, polyglycerol esters of fatty acids, acid and ester ethoxylates of fatty acids, sorbitan esters of fatty acids, transesterification products of natural or hydrogenated vegetable oil triglycerides and polyalkylene polyol, alcohol ethoxylates, polyoxyethylene or polyoxypropylene copolymers, phospholipids, polyoxyethylene sorbitan fatty acid derivatives (such as polysorbates, e.g., polysorbate 80), castor oil or hydrogenated castor oil ethoxylates, for example Polyoxyl 35 castor oil/Cremophor EL™, anionic surfactants, such as sodium lauryl sulphate or sodium oleate, alkylphenol surfactants, as well as mixtures of such surfactants. In such combinations, the surfactant may act to assist uptake of the fatty acid from the intestinal lumen. In one embodiment, a hydrophilic surfactant with an HLB value >10, such as Cremophor EL™, is used, optionally in combination with a co-surfactant, which may be a hydrophobic surfactant with a HLB value <10.

Typically, the vehicle comprises a lipid selected from olive oil, soybean oil, omega 3 oils, glycerol monooleate, and any combination of any of the foregoing. In one embodiment, the vehicle comprises olive oil and glycerol monooleate. In another embodiment, the vehicle comprises soybean oil and glycerol monooleate. In yet another embodiment, the vehicle comprises omega 3 oil and glycerol monooleate.

When, the vehicle comprises a surfactant it is typically selected from polysorbate 80, polyoxyl 35 castor oil, and any combination of any of the foregoing.

In an embodiment, the vehicle comprises (a) the lipids olive oil and glycerol monooleate and (b) the surfactant polyoxyl 35 castor oil.

In a preferred embodiment, the vehicle comprises (a) the lipids soybean oil and glycerol monooleate, and (b) the surfactant polyoxyl 35 castor oil.

In another preferred embodiment, the vehicle comprises (a) the lipids olive oil and glycerol monooleate, and (b) the surfactants polysorbate 80 and polyoxyl 35 castor oil.

In a further embodiment, the vehicle comprises a mixture of (a) long chain lipids, and (b) surfactants (hydrophilic surfactants). The weight ratio of (a):(b) may range from about 8:1 to about 1:6. For instance, the weight ratio of (a):(b) may be from about 4:1 to about 1:2. In one embodiment, the weight ratio of (a):(b) ranges from about 3:1 to about 1:2. In another embodiment, the weight ratio of (a):(b) ranges from about 2:1 to about 1:1. In one preferred embodiment, the weight ratio of (a):(b) is about 3:2.

The vehicle is preferably present in an amount sufficient to enhance or promote lymphatic transport of the lipophilic compound. See Porter et al., Pharm. Res. 20(9):1460-1465 (2003). In one embodiment, the fat component is present in an amount of at least about 500 mg. For example, the amount can be from about 0.05 to about 4 g, such as from about 0.1 to about 1 g, corresponding to an amount which could be readily incorporated into a single solid oral dosage form. In another embodiment, the fat component is present in an amount that is at least about 600 mg, for example, from about 600 mg to about 1200 mg or from about 600 mg to about 1000 mg. In a further embodiment of the fat component is present in an amount that is at least 500 mg to 10 g. Such as from 1500 mg to 10 g, 2000 mg to 8 g, 3000 mg to 7 g, 4000 mg to 6 g, or from 2000 mg to 6 g.

The vehicle may be formulated as lipid based emulsions or micro emulsions, or self-emulsifying or self-micro emulsifying formulations. Self-emulsifying and self-micro emulsifying formulations are those which spontaneously form emulsions or micro emulsions on contact of the contents of the solid oral dosage form with the gastric or intestinal fluids and which are commonly termed self-emulsifying drug delivery systems (SEDDS) or self-micro emulsifying drug delivery systems (SMEDDS). The lipophilic compound is intended to be solubilized in the vehicle either before or after adsorbing of the vehicle into the oral dosage form.

The Solid Carrier

The solid carrier, that is the granulate, can be compressed in the form of a tablet that comprises an adsorbent excipient, that is silicon dioxide, and optionally binder(s) and/or a disintegrant. The solid tablet may be inert or alternatively the solid tablet may have incorporated the lipophilic compound in part or fully. The solid carrier can be in the form of a tablet. The solid carrier is capable of adsorbing a vehicle.

When the solid carrier is in the form of granules, the median particle size of the granules may range from about 5 microns to about 600 microns, for example from about 10 to about 300 microns. Granules may be compressed to form a tablet which is used as the solid carrier.

The Adsorbent Excipient

The adsorbent excipient typically forms the bulk of the solid carrier. The adsorbent excipient (and the solid carrier) has a porosity of, for example, greater than about 10% v/v, such as greater than about 15% v/v, greater than about 20% v/v, greater than about 30% v/v or greater than about 30% v/v. In a preferred embodiment, the porosity is greater than about 30% v/v, for example, from about 30 to about 50% v/v.

In another embodiment, the porosity is up to about 97% (e.g., from about 90 to about 94%) (such as Zeofree 5170 or Aeroperl 300).

The adsorbent excipient may have a median particle size of from about 5 microns to about 600 microns, for example from about 10 to about 300 microns. In one embodiment, the porous excipient may have a particle size of from about 10 microns to about 150 microns.

The solid carrier may include the adsorbent excipient at a concentration of about 20% w/w or more, such as about 25% w/w or more, about 30% w/w or more, about 35% w/w or more, about 40% w/w or more, about 45% w/w or more, about 50 w/w or more, about 60% w/w or more, about 70% or more, about 80% or more, about 90% or more, about 95% or more, or about 98% or more. In additional embodiments, the adsorbent excipient is present at a concentration of from about 20% to about 95% w/w, such as from about 30% to about 90% w/w, from about 50% to about 90% w/w, from about 60% to about 90% w/w, from about 70% to about 90% w/w, from about 65% to about 85% w/w, from about 75% to about 85% w/w or from about 70% to about 80% w/w, based on 100% total weight of the solid carrier.

Many adsorbent excipients are found in the group of metal oxides and metal silicates. It was found that silicon dioxide was more inert to the added active ingredients compared to other adsorbent excipients.

Silicon dioxide however does not compress well and even for the skilled person it is not easy to produce tablets with high levels of silicon dioxide. High levels of adsorbent excipient will be needed to adsorb the amount of liquid needed for this invention. Part of the invention is therefore the selection of appropriate excipients to improve on the poor compressibility of silicon dioxide to be able to produce high-level silicon dioxide tablets without cracking and capping. To achieve this, a very long list of binder excipients have been tested at relevant levels. Most of these formulations produced tablets with capping and poor cohesive properties with the result of tablets falling apart. The examples of solid carries given in this paper demonstrate the preferred binding excipients for the use with silicon dioxide.

In a preferred embodiment, the adsorbent excipient is a silicon dioxide, such as Zeofree 5170 (available from J.M. Huber Corporation) or Aeroperl (available from Evonik industries).

Additional Excipients

The solid core of the oral dosage form, such as tablet, may further comprise one or more pharmaceutically acceptable excipients. Examples of such excipients include, but are not limited to, fillers, diluents, binders, lubricants, glidants, enhancers, wetting agents, surfactants, antioxidants, metal scavengers, pH-adjusting agents, acidifying agents, alkalizing agents, preservatives, buffering agents, chelating agents, stabilizing agents, coloring agents, complexing agents, emulsifying and/or solubilizing agents, absorption enhancing agents, modify release agents, flavoring agents, taste-masking agents, humectants, and sweetening agents.

Examples of suitable fillers, diluents and/or binders include lactose (e.g. spray-dried lactose, α-lactose, β-lactose), microcrystalline cellulose, hydroxypropylcellulose, hydroxypropyl methylcellulose (HPMC), methylcellulose, hydroxyethylcellulose, sodium carboxymethylcellulose, carboxymethylene, carboxymethylhydroxyethylcellulose and other cellulose derivatives, sucrose, agarose, sorbitol, mannitol, dextrins, maltodextrins, starches or modified starches (including potato starch, maize starch and rice starch), calcium phosphate (e.g. basic calcium phosphate, calcium hydrogen phosphate, dicalcium phosphate hydrate), calcium sulfate, calcium carbonate and potassium hydrogen phosphate.

Examples of metal scavengers include, but are not limited to, tartaric acid, citric acid, oxalic acid, EDTA and salts thereof, and DPTA (diethylenetriaminepentaacetic acid) and salts thereof.

Examples of antioxidants include, but are not limited to, BHT, BHA, propyl gallate, tocopherols, TBHQ (t-butyl hydroquinone), and ascorbyl palmitate.

Examples of diluents include, but are not limited to, calcium carbonate, dibasic calcium phosphate, tribasic calcium phosphate, calcium sulfate, microcrystalline cellulose, powdered cellulose, dextrans, dextrin, dextrose, fructose, kaolin, lactose, mannitol, sorbitol, starch, pregelatinized starch, sucrose, and sugar.

Examples of binders include, but are not limited to, acacia, alginic acid, agar, calcium carrageenan, sodium carboxymethylcellulose, microcrystalline cellulose, dextrin, ethylcellulose, gelatin, liquid glucose, guar gum, hydroxypropyl methylcellulose, methylcellulose, pectin, PEG, povidone, maltodextrin and pregelatinized starch.

Examples of glidants and lubricants include, but are not limited to, stearic acid, magnesium stearate, calcium stearate or other metallic stearate, talc, waxes and glycerides, light mineral oil, PEG, glyceryl behenate, colloidal silica, hydrogenated vegetable oils, corn starch, sodium stearyl fumarate, polyethylene glycols, alkyl sulfates, sodium benzoate, and sodium acetate.

Examples of antioxidants include, but are not limited to, ascorbic acid, ascorbyl palmitate, butylated hydroxyanisole, butylated hydroxytoluene, hypophosphorous acid, monothioglycerol, potassium metabisulfite, propyl gallate, sodium formaldehylde sulfoxylate, sodium metabisulfite, sodium thiosulfate, sulfur dioxide, tocopherol, tocopherol acetate, tocopherol hemisuccinate, and TPGS or other tocopherol derivatives. The concentration of an antioxidant and/or a stabilizing agent in the tablet may be, for example, from about 0.1% w/w to about 5% w/w (based upon 100% total weight of the tablet without any adsorbed compound and lipids/vehicles).

Examples of disintegrants include, but are not limited to, croscarmellose sodium, crospovidone, low-substituted Hydroxypropyl cellulose (L-HPC), polacrilin potassium, carboxymethylcellulose sodium, carboxymethylcellulose calcium, sodium alginate, sodium starch glycolate, starch or starch pregelatinized.

Solid Oral Dosage Form

The amount of solid carrier in the solid oral dosage form may vary depending on its porosity, as the liquid formulation. The solid dosage form preferably includes at least 600 mg of fats (lipids) and sufficient surfactants to allow for lymphatic absorption in the fasted state.

Since the solid oral dosage form, such as tablet or capsule, is intended for oral ingestion by a mammal, such as a human subject, the solid oral dosage form preferably weighs from about 50 mg to about 5000 mg, such as from about 200 mg to about 2000 mg, or from about 600 mg to about 1500 mg. In one embodiment, the solid oral dosage form weighs from about 700 mg to about 1200 mg.

The solid oral dosage form (e.g., oral tablet) described herein may optionally contain one or more coatings, such as a sub-coating and/or modified release coating (e.g. an enteric coating). The sub-coating may be, e.g., Opadray AMB OY-B. The enteric coating may contain, e.g., Acryl EZE, dimethicone and triethyl citrate.

In one embodiment, the solid oral dosage form does not have a coating. In a preferred embodiment, the solid oral dosage form does not have an enteric coating. In another embodiment, the solid oral dosage form does not have a modified release coating. In a preferred embodiment, the solid oral dosage form provides immediate release of the drug or drug derivative. In yet another embodiment, the solid oral dosage form provides extended release of the drug or drug derivative.

The solid oral dosage form may be in the form of a tablet. In one embodiment, the tablet is a compressed or molded tablet, e.g., having a hardness of from about 20 N to about 150 N. The hardness of the tablet can be from about 30, 40, or 50 N to about 70, 80, 90 or 100 N.

The oral tablet may include one or more excipients, such as those mentioned above including, but not limited to, flavoring agents, lubricants, binders, preservatives, and disintegrants.

In another embodiment, the solid dosage form comprises granules of the solid carrier, lipophilic compound in the vehicle, and optionally other excipients. The granules may, for example, be filled into a capsule which is administered.

Preparation of the Solid Oral Dosage Forms

The solid oral dosage forms described herein may be formed by (i) preparation of the solid carrier, (ii) preparation of the vehicle, (iii) adsorbing the vehicle into the solid carrier and filling the granule into capsules.

In one embodiment, tablets of the present invention are prepared by (ix) preparation of the solid carrier, (iix) pressing the solid carrier and optionally disintegrants and/or other tablet excipients into adsorbable tablets, (iiix) preparation of the vehicle, (ivx) adsorbing the vehicle into the loadable tablets.

In one embodiment, the compound is part of the carrier, in another embodiment the compound is solubilized in the vehicle, and in a third embodiment the compound is partly in the carrier and partly solubilized in the vehicle.

The compound and vehicle together form a self-emulsifying drug delivery system (SEDDS) or a self-micro emulsifying drug delivery systems (SMEDDS).

Step (ix) may be carried out by mixing binder or spraying binder solution onto granules of the porous excipient, granulate the mixture in a high shear mixer and drying the granules to provide the granulate.

The carrier granulate may be mixed with tablet excipients, e.g. disintegrants, lubricants etc. and optionally the drug derivative and pressed into tablets.

Preparation of the vehicle is done my simply mixing the components and optionally the lipophilic compound until a clear solution appears.

Adsorption is performed by immersing the tablet into the vehicle in a surplus of the compound, the time period for adsorbing the drug derivative is controlled and may range from about 30 minutes to about 5 hours, such as from about 30 minutes to about 1 hour. Adsorption can also be achieved by pouring the calculated oil mixture onto a bed of tablets, e.g., rotating in some form of a drum In all of the methods above, the granulate comprising an adsorbent excipient and a release enhancing agent may be compacted, such as compressed or molded into a tablet that has a suitable hardness, such as a hardness of about 20 N or more, about 25 N or more, about 30 N or more, about 35 N or more, about 40 N or more, about 45 N or more, about 50 N or more, about 60 N or more, about 70 N or more, about 90 N or more, about 100 N or more. In one embodiment, the hardness of the tablet is from about 30 N to about 150 N, such as from about 30 N to about 100 N.

Definitions

The term "no food effect" and "absence of food effect" on oral bioavailability refers to when the 90 percent CI for the ratio of population geometric means between fed and fasted treatments, based on log-transformed data, is contained in the equivalence limits of 80-125 percent for AUC0-inf (AUC0-t when appropriate) and Cmax.

The term "fasted state" refers to a state of the subject, such as mammal or human, in which the only lipids, if any, present in the intestine of the subject, apart from any which may have been included in a formulation according to the invention, are endogenous lipids. A reference to the oral administration of a drug or formulation according to the invention to a subject "in the fasted state" is a reference to the oral administration into the digestive system of the subject such that during the uptake into the lymphatic system of a therapeutically effective amount of the drug, the subject is in the fasted state. This generally means that the subject has not taken a meal at least 3 to 4 hours prior to the administration and, depending on the rate of uptake and the efficacy of the drug, no food is taken from 1 to 6 hours after the meal.

The term "fed state" as used herein refers to any state of the subject other than a "fasted state" as described above.

The term "log P" refers to the partition coefficient of a substance. The log P of a substance is the base ten logarithm of the ratio of solubility of the substance in n-octanol to solubility of the substance in water.

The term "HLB" or "HLB value" of a surfactant refers to the Hydrophilic-Lipophilic Balance and is a measure of the degree to which it is hydrophilic or lipophilic, determined by calculating values for the different regions of the molecule. For non-ionic surfactants the HLB=20*Mh/M, where M is the molecular mass of the whole molecule and Mh is the molecular mass of the hydrophilic portion of the Molecule. An HLB value of 0 corresponds to a completely lipophilic/hydrophobic molecule, and a value of 20 corresponds to a completely hydrophilic/lipophobic molecule. HLB values ≥10 describes a hydrophilic surfactant.

The term "production of endogenous lipid" as used herein refers to the biosynthesis within the intestinal absorptive cells of lipids, including mono, di or triglycerides and phospholipids, from bio-precursors, which bio-precursors could themselves be lipids or lipid conjugates, such as glycerides. For example the biosynthesis may involve the conversion of a lipid species unable to promote transport of the drug into the lymphatic transport system into a species which can. The term "production of endogenous lipid" may also refer to the translocation of lipid species into the enterocytes from elsewhere, such that the lipid species, or lipid metabolite thereof, is capable of promoting transport of the drug into the lymphatic transport system.

The term "mammal" or "mammal subject" as used herein (are interchangeable) refers to all sorts of mammals, such as humans, horses, pigs, dogs, cats, sheeps, etc.

All references, including publications, patent applications and patents, cited herein are hereby incorporated by reference to the same extent as if each reference was individually and specifically indicated to be incorporated by reference and was set forth in its entirety herein.

All headings and sub-headings are used herein for convenience only and should not be construed as limiting the invention in any way.

Any combination of the above-described elements in all possible variations thereof is encompassed by the invention unless otherwise indicated herein or otherwise clearly contradicted by context.

Recitation of ranges of values herein are merely intended to serve as a short method of referring individually to each separate value falling within the range, unless other-wise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about", where appropriate).

All methods described herein can be performed in any suitable order unless other-wise indicated herein or otherwise clearly contradicted by context.

The terms "a" and "an" and "the" and similar referents as used in the context of de-scribing the invention are to be construed to cover both the singular and the plural, unless otherwise indicated herein or clearly contradicted by context. Thus, "a" and "an" and "the" may mean at least one, or one or more.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

This invention includes all modifications and equivalents of the subject matter re-cited in the aspects or claims presented herein to the maximum extent permitted by applicable law.

The features disclosed in the foregoing description may, both separately and in any combination thereof, be material for realizing the invention in diverse forms thereof.

EXAMPLES

Further description of the present invention will now be done by the following non-limiting examples. It should be kept clearly in mind that the examples are merely illustrative of the present invention and should not be construed as limiting the scope of the invention in any way, as many variations and equivalents that are encompassed by the present invention will become apparent to those skilled in the art upon reading the present disclosure.

Example 1: Preparation of Oral SEDDS Formulations for Lymphatic Targeting

Six oral SEDDS formulations were prepared as summarized in Table 1.

TABLE 1

| SEDDS formulations for lymphatic targeting | |
|---|---|
| Formulation | Summary of Components |
| S1 | Olive oil: Glycerol Mono-Oleate 1:3 with Polysorbate 80: Polyoxyl 35 castor oil 1:1, 60% fat |
| S2 | Soybean oil: Glycerol Mono-Oleate 1:1 with Polyoxyl 35 castor oil, 60% fat |
| S3 | Soybean oil: Glycerol Mono-Oleate 1:1 with Polyoxyl 35 castor oil, 80% fat |
| S4 | Olive oil: Glycerol Mono-Oleate 65:35 with Polysorbate 80: Polyoxyl 35 castor oil 1:1, 60% fat |
| S5 | Glycerol Mono-Oleate with Polyoxyl 35 castor oil, 60% fat |
| S6 | Soybean oil: Glycerol Mono-Oleate 1:1 with Polyoxyl 35 castor oil, 70% fat |

The Six different SEDD systems were prepared as shown below in Table 2:

TABLE 2

| | Placebo SEDDS compositions | | | | | |
|---|---|---|---|---|---|---|
| | Formulation | | | | | |
| Ingredient | S1 | S2 | S3 | S4 | S5 | S6 |
| SEDDS | | | | | | |
| Olive oil | 9.00 | — | — | 34.4 | — | — |
| Soybean oil | — | 54.0 | 18.0 | — | — | 54.0 |
| Glycerol Mono-Oleate | 27.0 | 54.0 | 18.0 | 12.6 | 36.0 | 54.0 |
| Polysorbate 80 | 12.0 | — | — | — | — | — |
| Polyoxyl 35 castor oil | 12.0 | 72.0 | 9.0 | 24.0 | 24.0 | 46.3 |
| Total | 60.0 | 180.0 | 45.0 | 60.0 | 60.0 | 154.3 |

In each case, the oil components were dispersed and mixed to achieve a clear mono-phasic placebo vehicle system. Active lipophilic compound is added and dissolved in the placebo SEDD formulations.

Example 2: Solid Tablet Formulations

The Solid Carrier

The Solid Carrier was produced by mixing silicon dioxide (Zeofree 5170) with microcrystalline cellulose (Avicel PH 301) or low-substituted hydroxypropyl cellulose (L-HPC LH-21), and then granulate the mixture with a solution of Maltodextrin (Lycatab DSH) plus adequate amount of water in a high shear mixer. After granulation the granules were dried in a fluid-bed and sieved.

The carrier composition is given in Table 3.

TABLE 3

| | Solid carriers | | | | | |
|---|---|---|---|---|---|---|
| Raw Material | Carrier A Weight % | Carrier B Weight % | Carrier C Weight % | Carrier D mg/tablet | Carrier E mg/tablet | Carrier F mg/tablet |
| Silicon dioxide (Zeofree 5170) | 80.0 | 75.0 | 75.0 | 80.0 | 60.0 | 60.0 |
| Microcrystalline cellulose (Avicel PH301) | 5.0 | 10.0 | — | — | — | 10.0 |
| L-HPC LH-21 | — | — | 5.0 | 5.0 | — | — |
| Maltodextrin (Lycatab DSH) | 15.0 | 15.0 | 20.0 | 15.0 | 40.0 | 30.0 |
| Total | 100.0 | 100.0 | 100.0 | 100.0 | 100.0 | 100.0 |

Inactive Carrier Tablets

Solid carrier prepared as described was mixed with 5% to 15% of disintegrant for 10 minutes. Then 0.5% magnesium stearate was added and mixed for 5 minutes. The mixture was compressed into tablets on a 10×22 mm oval tooling using a Diaf tablet press. The tablet weight was between 800 mg and 1200 mg to fit the desired size and adsorption capacity of the tablets. The tablet composition is given in Table 4. The tablet hardness was 25N to 50 N.

TABLE 4

| | Carrier tablets | | | | | |
|---|---|---|---|---|---|---|
| Raw Material | Weight % | Weight % | Weight % | Weight % | Weight % | Weight % |
| Solid carrier A | 84.5 | — | — | — | | |
| Solid carrier B | — | 89.5 | — | — | | |
| Solid carrier C | — | — | 89.5 | — | | |

TABLE 4-continued

| | Carrier tablets | | | | | |
|---|---|---|---|---|---|---|
| Raw Material | Weight % | Weight % | Weight % | Weight % | Weight % | Weight % |
| Solid carrier D | — | — | — | 84.5 | | |
| Solid carrier E | | | | | 89.5 | |
| Solid carrier F | | | | | | 84.5 |
| L-HPC LH-11 | 15.0 | 10.0 | 10.0 | 15.0 | — | — |
| Croscarmellose sodium (AcDiSol) | — | — | — | — | 10.0 | 5.0 |
| Microcrystalline cellulose (Avicel PH102) | — | — | — | — | — | 10.0 |
| Magnesium stearate | 0.50 | 5.00 | 0.50 | 0.50 | 0.50 | 0.50 |
| Total | 100% | 100% | 100% | 100% | 100% | 100% |

Example 3: Solid Oral Dosage Forms

All solid dosage forms were prepared to contain 600 mg of long chain lipid.
(a) Carrier tablets: Tablet adsorbing was achieved by immersing the carrier tablets in the SEDDS vehicle. 20 tablets of each formulation were sorted to ensure homogeneity, and adsorbed in a 3 liter beaker by floating the tablets in an excess of the SEDDS vehicle and allowing the vehicle to be absorbed into the tablet. Adsorption was continued until the desired amount of SEDDS had been adsorbed. (1000 mg SEDDS for 60% fat SEDDS formulations and 750 mg SEDDS for 80% fat SEDDS formulations)
(b) Capsules: The active SEEDS were dispensed into an empty gelatin capsule shell by a pipette and the capsules were closed.

Example 4: Carrier Tablet Formulations

The Solid Carrier

The Solid Carrier was produced by mixing Colloidal Silicon dioxide (Aeroperl 300) with 10% microcrystalline cellulose (Avicel PH 101) and 5% Hypromellose (Metolose 90SH-100SR), and then granulate the mixture with a solution of 5% Hypromellose (Metolose 90SH-100SR) plus adequate amount of water in a high shear mixer. After granulation the granules were dried in a fluid-bed and sieved.

In the case that an antioxidant is needed to stabilize the active ingredient to be adsorbed, the antioxidant was added (as a 0.2% solution in ethanol) to the binder solution before it was added to the granulation.

The carrier composition is given in Table 5.

TABLE 5

| | Solid carriers | | | |
|---|---|---|---|---|
| Raw Material | Carrier G Weight % | Carrier H Weight % | Carrier I Weight % | Carrier J Weight % |
| Silicon dioxide (Aeroperl 300) | 80.0 | 70.0 | 69.95 | 69.95 |
| Microcrystalline cellulose (Avicel PH101) | 10.0 | 20.0 | 20.0 | 20.0 |
| Hypromellose (Metolose 90SH-100SR) | 10.0 | 10.0 | 10.0 | 10.0 |
| Ascorbyl palmitate | — | — | 0.05 | — |
| Butylated hydroxytoluoene | — | — | — | 0.05 |
| Total | 100.0 | 100.0 | 100.0 | 100.0 |

Carrier Tablets

Solid carrier prepared as described was mixed Microcrystalline cellulose and/or with 2%-5% of croscarmellose sodium for 10 minutes. Then 0.5% magnesium stearate was added and mixed for 5 minutes. The mixture was compressed into tablets on a 10×22 mm oval tooling using a Diaf tablet press. The tablet composition is given in Table 6. The tablet hardness was 34N.

TABLE 6

| | Carrier tablet compositions | | | |
|---|---|---|---|---|
| Raw Material | Weight % | Weight % | Weight % | Weight % |
| Solid carrier G | 70.0 | — | — | — |
| Solid carrier H | — | 97.5 | — | — |
| Solid carrier I | — | — | 70.0 | — |
| Solid carrier J | — | — | — | 97.5 |
| Microcrystalline cellulose (Avicel PH102) | 24.5 | — | 24.5 | — |
| Croscarmellose sodium (Ac-Di-Sol) | 5.0 | 2.0 | 5.0 | 2.0 |
| Magnesium stearate | 0.5 | 0.5 | 0.5 | 0.5 |
| Total | 100% | 100% | 100% | 100% |

The carrier tablets were loaded with SEDDS as described in Example 3.

Example 5: Tablets Containing an Active Ingredient

The Active Solid Carrier

Active solid carrier is prepared by dissolving Abiraterone Acetate in SEDDS S2 (see Table 9) (5% concentration), mixing Silicon dioxide (Zeofree 5170) with 40% maltodextrin (Lycatab DSH) and moistening the mixture with the Abiraterone Acetate solution and adequate amount of water in a high shear mixer. After granulation the granules are dried on trays and sieved.

The carrier composition is given in Table 7.

TABLE 7

| | Solid carriers | |
|---|---|---|
| | Active Solid carrier | |
| Raw Material | Weight % | mg/tablet |
| Silicon dioxide (Zeofree 5170) | 54.8 | 526.2 |
| Maltodextrin (Lycatab DSH) | 36.5 | 350.8 |
| Abiraterone Acetate | 0.4 | 4.0 |
| SEDDS S2 | 8.3 | 80.0 |
| Total | 100.0 | 961.0 |

Tablets Containing Abiraterone Acetate

For full amount of Abiraterone Acetate in loadable core tablet: Solid carrier E prepared as described in Example 2 was mixed with 2% of croscarmellose sodium and Abiraterone Acetate for 10 minutes. Then 0.5% magnesium stearate was added and mixed for 5 minutes. The mixture was compressed into tablets on a 10×22 mm oval tooling using a Diaf tablet press.

For partial amount of Abiraterone Acetate in loadable core tablet: Active Solid carrier prepared as described was mixed with 2% of croscarmellose sodium for 10 minutes. Then 0.5% magnesium stearate was added and mixed for 5 minutes. The mixture was compressed into tablets on a 10×22 mm oval tooling using a Diaf tablet press.

TABLE 8

Loadable tablets

| Raw Material | Abiraterone Acetate fully in tablet core | | Abiraterone Acetate partly in tablet core | |
|---|---|---|---|---|
| | Weight % | mg/tablet | Weight % | mg/tablet |
| Solid carrier granulate | 93.40 | 877.0 | | |
| Active Solid carrier granulate | | | 97.77 | 961.0 |
| Croscarmellose (Ac-Di-Sol) | 1.87 | 17.54 | 1.78 | 17.54 |
| Abiraterone Acetate | 4.26 | 40.00 | | |
| Magnesium stearate | 0.47 | 4.39 | 0.45 | 4.39 |
| Total | 100% | 938.9 | 100% | 982.9 |

SEDDS Vehicles

Two SEDDS vehicles (S2 and S2A) are prepared to be adsorbed into the carrier tablets, as shown below in Table 9:

TABLE 9

SEDDS formulations

| Ingredient | S2 | S2A |
|---|---|---|
| Olive oil | | |
| Soybean oil | 18.0 | 18.0 |
| Glycerol Mono-Oleate | 18.0 | 18.0 |
| Polysorbate 80 | | |
| Polyoxyl 35 castor oil | 24.0 | 24.0 |
| Abiraterone Acetate | — | 1.60 |
| Total | 60.0 | 61.60 |
| API conc. in SEDDS | — | 3.85% |

In each case, the oil components were dispersed and mixed to afford a clear mono-phasic placebo vehicle system. For the S2A vehicle, Abiraterone Acetate was dispersed and dissolved into the vehicle system overnight.

Solid Oral Dosage Form

All solid dosage forms were prepared to contain 40 mg of Abiraterone Acetate and 600 mg of long chain lipid. The solid dosage forms were prepared as follows Loadable tablets: Tablet adsorption was achieved by immersing the loadable tablets in the SEDDS vehicle. 20 tablets of each formulation were sorted to ensure homogeneity, and adsorbed in a 3 liter beaker by floating the tablets in an excess of the SEDDS vehicle and allowing the vehicle to be absorbed into the tablet.

TABLE 10

Active Solid Oral Dosage Forms

| | Formulation per solid dosage form | |
|---|---|---|
| Ingredient | A1 | A2 |
| Active SEDDS S2A | 956 mg | |
| Inactive SEDDS S2 | | 1000 mg |
| Partly active loadable tablets | 1 tablet | |
| Active loadable tablets | | 1 tablet |

Example 6: Stability Study of Silicon Dioxide Compared to a Magnesium Aluminometasilicate In double experiments, 1 ml of Soybean oil based SEEDS (corresponding to S2 in Example 1) containing 40 mg Testosterone Undecanoate was added to samples of either magnesium aluminometasilicate (Neusilin NS2N granules) or silicon dioxide. The samples were placed at 40° C./75RH in closed glass vial for 1 month in a stability chamber. Following stability storage, the samples were dissolved in 3 mL heptane, following 3 mL 2-propanol and taken to 25 mL with methanol. The samples were analyzed by HPLC using a Kinetex C18 column (50×4.6 mm) 5 μm, column temperature 30° C., mobile phase: 5% water in methanol, flow 1.5 ml/min at a wavelength 260 nm. The chromatograms showed two (2) testosterone undecanoate related impurities that were significantly more abundant in the magnesium aluminometasilicate compared to the silicon dioxide.

TABLE 11

Testosterone related impurities after storage at 40° C./75 RH after 1 month of two (2) different tablet excipients silicon dioxide and magnesium aluminometasilicate.

| | Impurity RT 3.75 | Impurity RT 3.95 |
|---|---|---|
| SEEDS in Silicon dioxide. Sample no 1. | 0.29 | 0.15 |
| SEEDS in Silicon dioxide. Samples no. 2 | 0.39 | 0.19 |
| Average (n = 2) | 0.34 | 0.17 |
| SEEDS in Magnesium aluminiometasilicate. Sample no. 1. | 1.39 | 1.35 |
| SEEDS in Magnesium aluminiometasilicate. Sample no. 2. | 1.37 | 1.34 |
| Average (n = 2) | 1.38 | 1.35 |

Example 7: Tablets Containing Abiraterone Acetate

The Solid Carrier was produced by mixing Colloidal Silicon dioxide (Aeroperl 300) with Butylated hydroxytoluene and then granulate the mixture with a solution of 12.5% Maltodextrin (Lycatab DSH) plus adequate amount of water in a high shear mixer. After granulation the granules were dried in a fluid-bed and sieved. Batch size was 700 g for a 6 L high shear mixer.

The carrier composition is given in Table 7.

TABLE 12

| Raw Material | Solid carrier K Weight % |
|---|---|
| Silicon dioxide (Aeroperl 300) | 79.9 |
| Maltodextrin (Lycatab DSH) | 20.0 |
| Butylated hydroxytoluene | 0.1 |
| Purified water | qs |
| Total | 100.0 |

Carrier Tablets

Solid carrier prepared as described was mixed with L-HPC LH11 for 10 minutes. Then 0.5% magnesium stearate was added and mixed for 5 minutes. The mixture was compressed into tablets on a 10×22 mm oval tooling using a Diaf tablet press. The tablet composition is given in Table 6. The tablet weight was approx. 850 mg and hardness was 30N.

TABLE 13

Carrier tablet compositions

| Raw Material | Weight % |
|---|---|
| Solid carrier K | 94.5 |
| L-HPC LH11 | 5.0 |
| Magnesium stearate | 0.5 |
| Total | 100% |

SEDDS Vehicle

SEDDS vehicle was prepared to be adsorbed into the carrier tablets, as shown below in Table 9:

TABLE 14

SEDDS formulations

| Ingredient | |
|---|---|
| Soybean oil | 18.0 |
| Glycerol Mono-Oleate | 18.0 |
| Polyoxyl 35 castor oil | 24.0 |
| Abiraterone Acetate | 1.025 |
| Total | 61.0 |
| API conc. in SEDDS | 2.5% |

In each case, the oil components were dispersed and mixed to afford a clear mono-phasic placebo vehicle system. Then Abiraterone Acetate was dispersed and dissolved into the vehicle system overnight.

Solid Oral Dosage Form

All solid dosage forms were prepared to contain 16.7 mg of Abiraterone Acetate and 400 mg of long chain lipid. The solid dosage forms were prepared as follows:

Loadable tablets: Tablet adsorption was achieved by immersing the loadable tablets in the SEDDS vehicle. 20 tablets of each formulation were sorted to ensure homogeneity, and adsorbed in a 3 liter beaker by floating the tablets in an excess of the SEDDS vehicle and allowing the vehicle to be absorbed into the tablet.

Capsules: Capsules were filled with SEDDS solution by a pipette.

TABLE 15

Active Solid Oral Dosage Forms

| | Formulation per solid dosage form | |
|---|---|---|
| Ingredient | A3 | A4 |
| Active SEDDS S2A | 683 mg | 683 mg |
| Inactive loadable tablets | | 1 tablet |
| Hard shell gelatin capsule | 1 capsule | |

Example 8: Stability Study on Effect of Additives Using Silicon Dioxide

Using the above formulation of silicon dioxide, soybean oil based SEDDS and testosterone undecnoate, it was investigated to stabilize the system further by addition of antioxidants (alpha-tocopherol, ascorbyl palmitate) and/or metal scavenger (EDTA). 0.1% EDTA disodium salt was dissolved in the granulation fluid and added to the carrier (Carrier K, table 5) and thereby to the carrier tablet (table 6). 0.02% alpha-Tocopherol and 0.025% Ascorbyl palmitate were dissolved in the SEDDS along with 40 mg Testosterone Undecanoate/1000 mg SEDDS (corresponding to S2 in Example 1). The samples were placed at 30° C./65RH in closed HdPE containers for 2 month in a stability chamber. Following stability storage, the samples were analyzed as described in example 6 by HPLC and for peroxides according to Ph. Eur.

TABLE 16

Stability effect of additives using silicon dioxide.

| | Impurity RRT 0.53 | Impurity RRT 0.59 | Peroxide value |
|---|---|---|---|
| SEEDS in Silicon dioxide. No antioxidants | 0.47 | 0.47 | 45.3 |
| SEEDS in Silicon dioxide. EDTA 0.1%, Tocopherol 0.02% | 0.04 | 0.04 | 1.9 |
| SEEDS in Silicon dioxide. EDTA 0.1%, Tocopherol 0.02% Ascorbyl palmitate 0.025% | 0.04 | 0.05 | 1.3 |
| SEEDS in Silicon dioxide. Tocopherol 0.04% Ascorbyl palmitate 0.025% | 0.14 | 0.12 | 29.2 |
| SEEDS in Silicon dioxide. Tocopherol 0.02% Ascorbyl palmitate 0.05% | 0.13 | 0.09 | 28.6 |

Example 9: Synthesis of C11-Paclitaxel and DHA-Paclitaxel 700 mg paclitaxel is dissolved in 500 ml dichloromethane. This solution is added 100 mg dimethylaminopyridine and 210 mg Diisopropylcarbodiimide. The solution is stirred and flushed with inert gas like nitrogen or argon. To the solution is added either 186 mg undecanoic acid or 328 mg docosahexaene acid and the solution is stirred under inert gas for 1 hour. The reaction mixture is then concentrated to 2-5 ml and applied a 30 g silica column for chromatographic purification using a 1:1 mixture of hexane and ethylacetate as eluent. Fractions of each approx. 5 ml eluate is collected and analyzed by HPLC for content of the esterified product. Fractions with high content of the reaction product is pooled and evaporated to dryness under inert air. The isolated products are immediately dissolved in SEDDs and kept under inert atmosphere until filled into capsules. Each capsule contains the derivative of paclitaxel in an amount corresponding to 10 or 12.5 mg of the parent compound i.e. paclitaxel. The products are used for the pharmacokinetic study in Beagle dogs as described in example 12.

Example 10: Single Dose Pharmacokinetic Study in Beagle Dogs in the Fasted State of C11-Paclitaxel and DHA-Paclitaxel The study is a randomized, balanced, single dose, crossover study in Beagle dogs comparing pharmacokinetics in fasted state to demonstrate an increased bioavailability, reduced variation in absorption of the C11-paclitaxel and DHA-paclitaxel.

The C11-paclitaxel and DHA-paclitaxel products prepared as described in example 9 is compared with an oral solution of the infusion concentrate of paclitaxel being the comparator. The total oral dosage provided is 75 mg calculated as parent compound.

The dogs are deprived of food from late afternoon the day prior dosing. Pentagastrin is dosed via IM (6 µg/kg, 200 µg/mL in water) 30 min prior to administration. Pentagastrin is administered to ensure low pH in the dog's stomach, which otherwise will not have an as low pH as in humans stomachs. Gastric pH is measured right before pentagastrin dosing and right before dosing of the abiraterone acetate formulations.

The capsule is put directly on the aditus laryngis of the dog to ensure that the tablet is not chewed but swallowed whole. The dogs receive totally 100 ml of water immediately following the dosing.

Blood samples (approximately ~0.5 mL) are taken from each animal at each dosing occasion on 10 time points up to 24 hours after dosing including a pre-dose.

The pharmacokinetic parameters calculated are i.e. total exposure, or area under the concentration-time curve (AUC0-inf, AUC0-t), peak exposure (Cmax), and time to peak exposure (Tmax).

Example 11: Single Dose Pharmacokinetic Study in Beagle Dogs in the Fasted and Fed State of Tablet Containing Abiraterone Acetate in SEDDS The study is a randomized, balanced, single dose, crossover study in Beagle dogs comparing pharmacokinetics in fasted and fed state, respectively to demonstrate an increased bioavailability, reduced variation in absorption well as a reduced or no food effect of the tablet with abiraterone acetate in the SEDDS.

A tablet containing Abiraterone acetate in SEDDS is compared to Zytiga® tablets (comparator product). Dogs receive a single dose of each product. In fasted state the dogs are deprived of food from late afternoon the day prior dosing. The dogs are fed 5 minutes prior to dosing in the fed state part of the study.

Pentagastrin is dosed via IM (6 µg/kg, 200 µg/mL in water) 30 min prior to administration. Pentagastrin is administered to ensure low pH in the dog's stomach, which otherwise will not have an as low pH as in humans stomachs. Gastric pH is measured right before pentagastrin dosing and right before dosing of the abiraterone acetate formulations.

The tablet is put directly on the aditus laryngis of the dog to ensure that the tablet is not chewed but swallowed whole. To ensure the complete oral dose is received, the dogs receive 100 mL of water immediately following the tablet dosing.

Blood samples (approximately ~0.5 mL) are taken from each animal at each dosing occasion on 10 time points up to 24 hours after dosing including a pre-dose.

The pharmacokinetic parameters calculated are i.e. total exposure, or area under the concentration-time curve (AUC0-inf, AUC0-t), peak exposure (Cmax), and time to peak exposure (Tmax). The variation in absorption is calculated and compared to that of Zytiga in both fed and fasted state.

Example 12: Single Dose Pharmacokinetic Study in Beagle Dogs in the Fasted State of C11-Paclitaxel and DHA-Paclitaxel Administered in SEDDS Formulation S2 in a Capsule The study was a randomized, balanced, single dose, parallel group study in Beagle dogs comparing pharmacokinetics in fasted state of capsules containing C11-paclitaxel and DHA-paclitaxel, respectively in SEDDS formulation S2 (see Table 1).

The C11-paclitaxel and DHA-paclitaxel products were prepared as described in example 8 and were compared to an oral solution 2 mg/ml of the infusion concentrate of paclitaxel being the comparator. The strength of each capsule was 12.5 mg of paclitaxel equivalents for the C-11 paclitaxel capsule and 10 mg of paclitaxel equivalents for the DHA-paclitaxel. The total oral dosage provided was 75 mg calculated as parent compound for paclitaxel and C11-paclitaxel, respectively and 60 mg calculated as parent compound for DHA-paclitaxel.

The dogs were deprived of food from late afternoon the day prior dosing. The capsule was put directly on the aditus laryngis of the dog to ensure that the capsule is not chewed but swallowed whole. All dogs received totally 100 ml of water immediately following the dosing.

Blood samples (approximately ~0.5 mL) were taken from each animal at each dosing occasion on 10 time points up to 24 hours after dosing including a pre-dose.

The pharmacokinetic parameters calculated are i.e. total exposure, or area under the concentration-time curve (AUC0-inf, AUC0-t), peak exposure (Cmax), time to peak exposure (Tmax), terminal half-life t1/2 and the conversion rate from prodrug to parent.

TABLE 17

Summary of major pharmacokinetic parameters of pro-drug or parent after oral dose at 75 mg paclitaxel equivalents/animal (paclitaxel and paclitaxel undecanoate) or 60 mg paclitaxel equivalents/animal (paclitaxel-DHA) in male beagle dogs (N = 4).

| Treatment Group | PK parameters | | | | | |
|---|---|---|---|---|---|---|
| | $C_{max}$ | $T_{max}$ | $t_{1/2}$ | $AUC_{0-t}$ | $AUC_{0-\infty}$ | $AUC_{0-t}$(parent)/ $AUC_{0-t}$(prodrug) |
| | ng/mL | hr | hr | hr * ng/mL | hr * ng/mL | % |
| PK parameters of prodrug | | | | | | |
| Paclitaxel undecanoate | 422[a] | 2.00 | 6.44 | 1778[b] | 1882[c] | |
| Paclitaxel-DHA | 63.8[d] | 4.50 | 6.33 | 402[e] | 643[f] | |
| PK parameters of paclitaxel | | | | | | |
| Paclitaxel | 148 | 2.50 | 13.7 | 771 | 973 | NA |
| Paclitaxel undecanoate | 2.26 | 8.00 | 19.6 | 24.3 | 52.0 | 1.48 |
| Paclitaxel-DHA | 10.4 | 2.25 | 11.6 | 73.3 | 97.2 | 22.3 |

Paclitaxel undecanoate: [a]Equivalent to 352 ng/mL of paclitaxel; [b]Equivalent to 1485 hr * ng/mL of paclitaxel; [c]Equivalent to 1572 hr*ng/mL of paclitaxel
Paclitaxel-DHA: [d]Equivalent to 46.8 ng/mL of paclitaxel; [e]Equivalent to 295 hr * ng/mL of paclitaxel; [f]Equivalent to 471 hr*ng/mL of paclitaxel Example 13: Single Dose Pharmacokinetic Study in Beagle Dogs in the Fasted and Fed State of a Tablet and a Capsule Containing Abiraterone Acetate in SEDDS Formulation S2

The study was a randomized, balanced, single dose, cross-over study in Beagle dogs comparing pharmacokinetics in fasted and fed state, respectively to demonstrate low variation in absorption well as a reduced or no food effect of the tablet and capsule, respectively containing abiraterone acetate in a SEDDS formulation S2 (see Table 1).

Dogs received 6 capsules or tablet of 16.7 mg corresponding to 100 mg of abiraterone acetate as a single dose. In fasted state the dogs were deprived of food from late afternoon the day prior dosing. The dogs were fed 30 minutes prior to dosing in the fed state part of the study.

Pentagastrin was dosed via IM (6 µg/kg, 200 µg/mL in water) 30 min prior to administration. Pentagastrin is administered to ensure low pH in the dog's stomach, which otherwise will not have an as low pH as in humans stomachs. Gastric pH was measured right before pentagastrin dosing and right before dosing of the abiraterone acetate formulations.

The tablets or capsules were put directly on the aditus laryngis of the dog to ensure that the products were not chewed but swallowed whole. To ensure the complete oral dose is received, the dogs received 100 mL of water immediately following the dosing.

Blood samples (approximately ~0.5 mL) were taken from each animal at each dosing occasion on 10 time points up to 24 hours after dosing including a pre-dose.

The pharmacokinetic parameters calculated are i.e. total exposure, or area under the concentration-time curve (AUC0-inf, AUC0-t), peak exposure (Cmax), time to peak exposure (Tmax) and terminal half-life t½. The variation in absorption was calculated in both fed and fasted state.

TABLE 18

Summary of major pharmacokinetic parameters of abiraterone after oral dose of abiraterone acetate at 100 mg/animal (N = 4/time point) in fasted state and with food.

| Treatment Group | PK parameters | | | | |
|---|---|---|---|---|---|
| | $C_{max}$ | $T_{max}$ | $t_{1/2}$ | $AUC_{0-t}$ | $AUC_{0-\infty}$ |
| | ng/mL | hr | hr | hr*ng/mL | hr*ng/mL |
| | PK parameters of abiraterone | | | | |
| Tablet-fasted | 38.0 | 2.63 | 3.83 | 193 | 202 |
| Capsule-fasted | 440 | 1.25 | 4.34 | 1218 | 1233 |
| Tablet-fed | 20.4 | 3.63 | 1.37 | 74.9 | 98.9 |
| Capsule-fed | 541 | 1.13 | 3.68 | 1132 | 1138 |

The CV % for $C_{max}$, $AUC_{0-t}$ and $AUC_{0-\infty}$ for the capsules were 23.4%, 10.4% and 10.5% in fasted state and 33.6%, 19.3% and 19.2% in fed state, respectively.

The CV % for $C_{max}$, $AUC_{0-t}$ and $AUC_{0-\infty}$ for the tablets were 21.7%, 16.1% and 16.6% in fasted state and 45.0%, 43.2% and 10.0% in fed state, respectively.

Example 14: Synthesis of Docosahexaenoic Acid Amide of Octreotide 400 mg octreotide and 45 mg dimethylaminopyridine is dissolved in 7 ml DMF. 200 µl diisopropylcarbodiimide is added. 163 mg hexacosanoic acid is dissolved in 9 ml chloroform slightly heated. The solutions are mixed and stirred for 1 hour. The reaction mixture is concentrated and transferred to a 15 g silicondioxide for column chromatography using hexane/ethylacetate 1/1. The product was further purified by filtering through a 3 g silicondioxide column with hexane/ethylacetate 1/1 and the eluate is collected and concentrated to dryness. The total yield is 440 mg octreotide ceroate corresponding to approx. 80% overall yield.

I claim:

1. A composition comprising: a lipophilic compound having a log P of at least 5, and a self-emulsifying vehicle, wherein:
    the self-emulsifying vehicle comprises (a) a fat component in an amount of at least 700 mg sufficient to achieve lymphatic absorption of the lipophilic compound in a mammal and to enhance or promote intestinal lymphatic transport of the lipophilic compound upon oral administration in a fasted state as well as in a fed state, compared to a composition without the fat component, wherein the fat component consists of mono-glycerides of long chain fatty acids and tri-glycerides of long chain fatty acids in a weight ratio of tri-glycerides to mono-glycerides from about 2.8:1 to about 1:5, wherein the long chain fatty acids in the monoglycerides are selected from fatty acid chains having from 14 to 24 carbon atoms and the long chain fatty acids in the triglycerides are selected from fatty acid chains having from 14 to 24 carbon atoms, and (b) a hydrophilic surfactant, wherein the weight ratio (a):(b) is from about 10:1 to about 1:2,
    the composition exhibits an AUC(0-inf) (fasted)/AUC(0-inf) (fed) of at least about 0.8, and
    the composition is a dosage form selected from the group consisting of a liquid, a gel, capsules, granules, and tablets.

2. The composition of claim 1, wherein the amount of the fat component is from 700 mg to 1000 mg.

3. The composition of claim 1, wherein the weight ratio of (a):(b) ranges from about 4:1 to about 1:2.

4. The composition of claim 1, wherein the long chain fatty acids in the monoglycerides are selected from linolenic acid, oleic acid, palmitic acid, linoleic acid, or stearic acid.

5. The composition of claim 1, wherein the long chain fatty acids in the triglycerides are selected from linolenic acid, oleic acid, palmitic acid, linoleic acid, or stearic acid.

6. The composition of claim 1, wherein the fat component comprising a triglyceride of long chain fatty acids is a naturally derived oil selected from soybean oil, olive oil, sesame oil, safflower oil, peanut oil, rapeseed oil, sunflower oil, coconut oil, corn oil, sunflower seed oil, cotton seed oil, palm oil, arachidis oil or any combination thereof.

7. The composition of claim 1, wherein the fat component is selected from mixtures of olive oil and glycerol mono oleate and mixtures of soybean oil and glycerol mono oleate.

8. The composition of claim 1, wherein the composition, upon dilution in purified water, forms droplets which a d50 of less than about 200 micrometer.

9. The composition of claim 1, wherein the composition is tablet, and the lipophilic compound is fully or partly in a solid core.

10. The composition of claim 9, wherein the self-emulsifying vehicle is adsorbed into the solid core.

11. The composition of claim 10, wherein the lipophilic compound is dissolved in the self-emulsifying vehicle and adsorbed into the solid core.

12. The composition of claim 1, wherein the composition is a tablet having a solid core comprising the lipophilic compound and the self-emulsifying vehicle absorbed into the solid core, wherein the at least 700 mg of fat component is an amount sufficient to enhance or promote intestinal lymphatic transport of the compound upon oral administration in the fasted state as well as in fed state, compared to a composition without the self-emulsifying vehicle component in said solid core.

13. The composition of claim 12, wherein the lipophilic compound is dissolved in the self-emulsifying vehicle and adsorbed into the solid core or wherein the lipophilic compound is partly or fully formulated into the solid core and then the self-emulsifying vehicle is adsorbed into the solid core.

14. The composition of claim 9, wherein the solid core has a porosity of at least 30% volume.

15. The composition of claim 14, wherein the solid core comprises a silicon dioxide in an amount of at least 40% by weight of the total composition without the lipophilic compound.

16. The composition of claim 1 being selected from a liquid, a gel, or a capsule comprising the lipophilic compound and the self-emulsifying vehicle in liquid form.

17. The composition of claim 1, wherein the hydrophilic surfactant is selected from hydrogenated castor oil ethoxylates, polysorbates or any other hydrophilic surfactant with a Hydrophile-Lipophile Balance (HLB) value of 10 or higher, and any combination thereof.

18. The composition of claim 1, wherein the lipophilic compound is selected from abiraterone acetate, acitretin, allylestrenol, alpha tocopherol, amidarone, aprepitant, atorvastatin, bexarotene, bromocriptine, candesartan, cinacalcet, clomiphene, diethyl stilbestrol, dihomo-gamma-linoleic acid, ebastine, ergocalciferol, fenofibrate, fucidic acid, halofantrine, irbesartan, isotretinoin, itraconazole, lapatinib, liraglutide, loratidine, nandrolone decanoate, nelfinavir, olmesartan, orlistat, posaconazole, probucol, raloxifene, ritonavir, tamoxifen, telmisartan, teprenone, tipranavir, valsartan, and zuclopenthixol.

19. The composition of claim 1, wherein the lipophilic compound is selected from a compound which has been modified by attachment of a lipophilic moiety to increase the lipophilicity of the lipophilic compound to log P of at least 5 making it suitable for lymphatic uptake.

20. The composition of claim 19, wherein the lipophilic compound is selected from paclitaxel docosahexaenoate, paclitaxel undecanoate, paclitaxel oleate and paclitaxel stearate; octreotide covalently attached to a fatty acid with at least 20 carbon atoms in an amide formation; leuprolide covalently attached to a fatty acid ester via the aliphatic or aromatic hydroxyl group present in the peptide; propofol covalently attached to a fatty acid ester via the phenolic aromatic hydroxy group; and testosterone undecanoate.

21. The composition of claim 1, wherein the fat component is a mixture of soybean oil and glycerol mono-oleate.

22. The composition of claim 19, wherein the lipophilic compound is paclitaxel undecanoate.

23. The composition of claim 1, wherein the composition is in a single dosage form selected from granules comprising the lipophilic compound and self-emulsifying vehicle or capsule comprising said granules.

24. The composition of claim 18, wherein the lipophilic compound is abiraterone acetate.

25. The composition of claim 1, wherein the composition is a single dosage form selected from the group consisting of a liquid, a gel, a capsule, granules, and a tablet.

* * * * *